United States Patent
Spohn et al.

(10) Patent No.: US 7,273,477 B2
(45) Date of Patent: Sep. 25, 2007

(54) SYRINGE INTERFACES AND SYRINGE ADAPTERS FOR USE WITH MEDICAL INJECTORS

(75) Inventors: Michael A. Spohn, Butler, PA (US); James Albert Dedig, Pittsburgh, PA (US); Glen P. Williams, Springdale, PA (US)

(73) Assignee: Medrad, Inc., Indianola, PA (US)

( * ) Notice: Subject to any disclaimer, the term of this patent is extended or adjusted under 35 U.S.C. 154(b) by 612 days.

(21) Appl. No.: 10/466,413

(22) PCT Filed: Jan. 18, 2002

(86) PCT No.: PCT/US02/01657

§ 371 (c)(1),
(2), (4) Date: Jul. 16, 2003

(87) PCT Pub. No.: WO02/056945

PCT Pub. Date: Jul. 25, 2002

(65) Prior Publication Data

US 2004/0116893 A1    Jun. 17, 2004

Related U.S. Application Data

(60) Provisional application No. 60/262,520, filed on Jan. 18, 2001.

(51) Int. Cl.
*A61M 31/00*    (2006.01)
(52) U.S. Cl. ...................... 604/500; 604/131
(58) Field of Classification Search ............ 604/152, 604/154, 151, 181, 500, 187, 140, 218, 227, 604/506, 507, 131; 128/DIG. 1, 12

See application file for complete search history.

(56) References Cited

U.S. PATENT DOCUMENTS

| 4,006,736 A | 2/1977 | Kranys et al. |
| 4,677,980 A | 7/1987 | Reilly et al. |
| 5,383,858 A | 1/1995 | Reilly et al. |
| 5,520,653 A | 5/1996 | Reilly et al. |

(Continued)

FOREIGN PATENT DOCUMENTS

| DE | 19621394 | 1/1998 |
| EP | 0919251 | 6/1999 |
| JP | 1997122234 | 5/1997 |

(Continued)

*Primary Examiner*—Nicholas D. Lucchesi
*Assistant Examiner*—Christopher D. Koharski
(74) *Attorney, Agent, or Firm*—Jill Denesvich; Gregory L. Bradley

(57) ABSTRACT

A syringe interface or adapter includes a first retaining member that pivots about an axis generally perpendicular to and offset from the axis of an injector piston when the syringe interface is attached to the injector. The first retaining member pivots in a rearward direction to engage a portion of the syringe flange. The syringe interface further includes a second retaining member slideably positioned within a passage in the syringe interface to slide in a direction generally perpendicular to the axis of the piston when the syringe interface is attached to the injector to engage a portion of the syringe flange. The first retaining member and the second retaining member preferably cooperate to engage the syringe flange around the entire perimeter of the syringe flange. The first retaining member is preferably biased toward an open position. The syringe interface can also include a rear portion having an attachment mechanism to attach the syringe interface to the injector.

22 Claims, 26 Drawing Sheets

U.S. PATENT DOCUMENTS

| | | | |
|---|---|---|---|
| 5,865,805 | A | 2/1999 | Ziemba |
| 5,913,844 | A | 6/1999 | Ziemba et al. |
| 5,938,639 | A * | 8/1999 | Reilly et al. ............... 604/131 |
| 6,312,410 | B1 * | 11/2001 | Yamamoto ............... 604/152 |
| 2001/0047153 | A1 | 11/2001 | Trocki et al. |
| 2003/0120212 | A1 | 6/2003 | Dedig et al. |

FOREIGN PATENT DOCUMENTS

| | | |
|---|---|---|
| WO | WO9736635 | 10/1997 |
| WO | WO01/08727 | 2/2001 |
| WO | WO0137903 | 5/2001 |
| WO | WO02/056947 | 7/2002 |

* cited by examiner

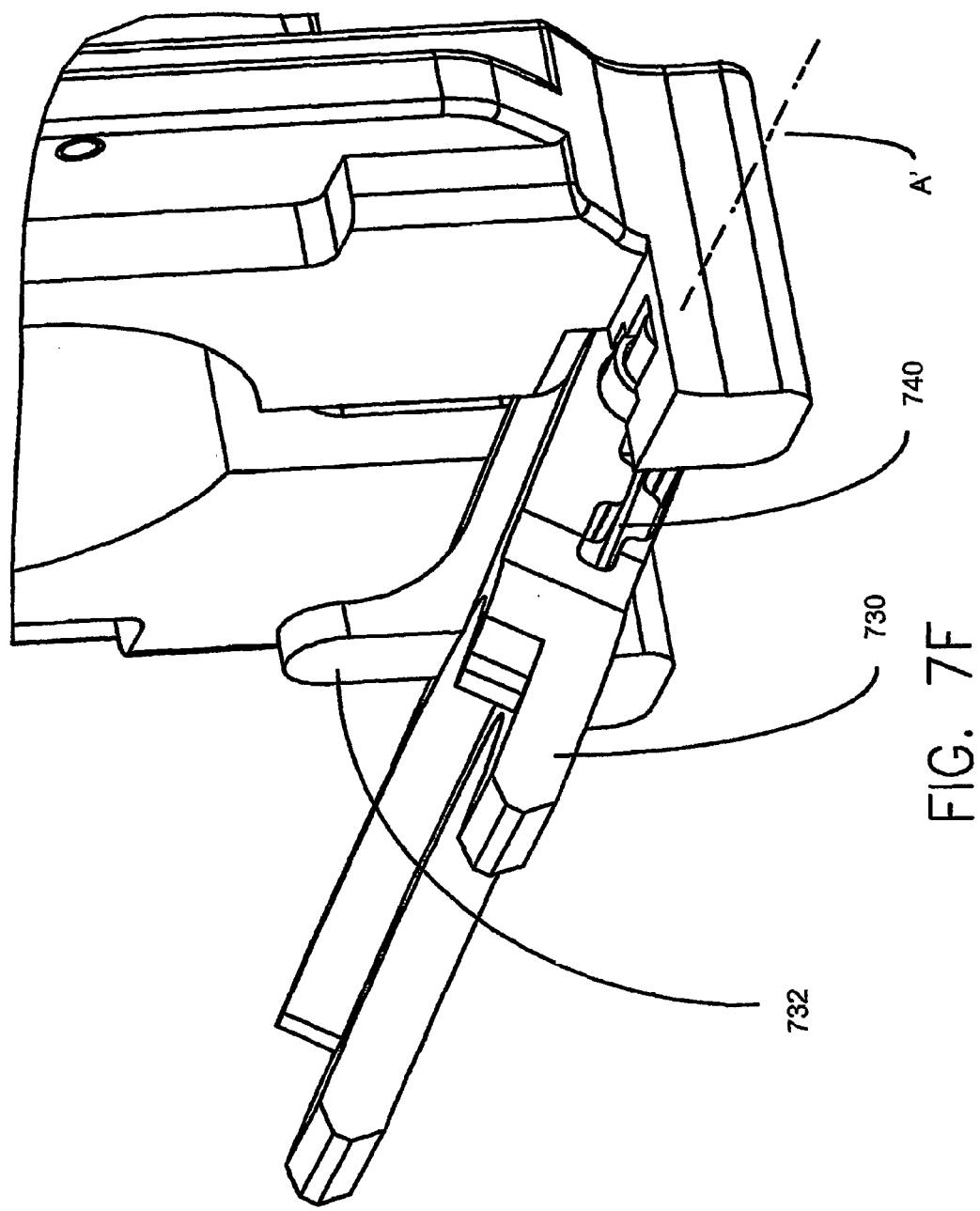

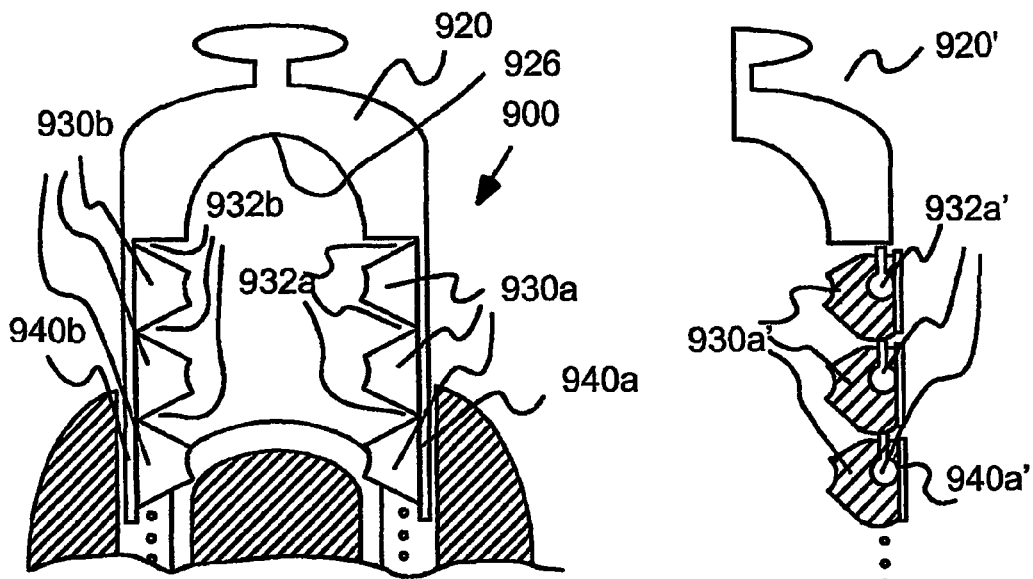
FIG. 10A
FIG. 11
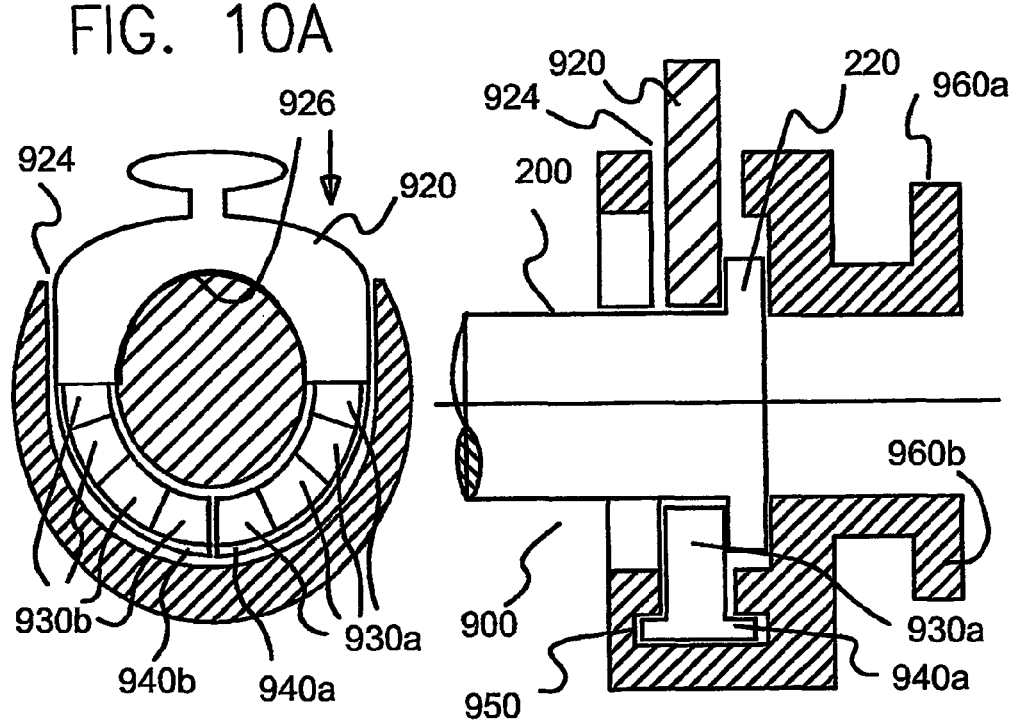
FIG. 10B
FIG. 10C

SYRINGE INTERFACES AND SYRINGE ADAPTERS FOR USE WITH MEDICAL INJECTORS

CROSS REFERENCE TO RELATED APPLICATIONS

This application is a national stage of International Patent Application No. PCT/US2002/001657, filed on Jan. 18, 2002, and claims the benefit of U.S. Provisional Application No. 60/262,520, filed on Jan. 18, 2001, the disclosures of which are incorporated by reference.

BACKGROUND OF THE INVENTION

The present invention relates generally to syringe interfaces and syringe adapters and, more particularly, to syringe interfaces and syringe adapters for use with medical injectors and to medical injector systems using such syringe interfaces and adapters.

A number of injector-actuated syringes and powered injectors for use in medical procedures such as angiography, computed tomography, ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

The front-loading injector of U.S. Pat. No. 5,383,858 includes a mounting mechanism for securing the syringe to the front wall of the injector. Other types of mounting mechanisms for front-loading syringes are disclosed in PCT Publication No. WO 01/37903 and U.S. patent application Publication No. 2001-47153, each assigned to the assignee of the present invention, the disclosures of which are incorporated herein by reference. Specifically designed mounting mechanisms generally prevent the use of syringes of other various types with front-loading injectors. Syringe adapters attachable to those front-loading injectors are sometimes used to allow the use of such syringes with the front-loading injectors.

For example, U.S. Pat. No. 5,520,653 discloses several adapters designed to allow the use of various syringes with a front-loading injector. In one embodiment, the adapter of U.S. Pat. No. 5,520,653 includes a syringe carrier having a front end, a rear end, and syringe-retaining channel located between the carrier front and rear ends for engaging at least a portion of the syringe flange. Mounting flanges near the rearward end of the carrier releasably mount the carrier in a desired position relative to the front wall of the injector. Likewise, Japanese Pat. Publication No. 09-122234 discloses another adapter that allows use of various syringes with a front-loading injector. In this adapter, a pair of pinching elements rotates to contact a portion of a syringe including a rear syringe flange and retain the syringe upon the adapter.

Although a number of syringe interfaces and adapters are currently available, it remains desirable to develop improved interfaces and adapters for use with syringes of various types to permit use of such syringes with medical or other injectors.

SUMMARY OF THE INVENTION

In general, the present invention provides syringe interfaces for removably or releasably attaching a syringe to an injector. The syringe interfaces or retaining members of the present invention can be permanently attached to an injector or can be attachable or removably attachable to an injector via an attachment mechanism (for example, to a different type of syringe interface on the injector). In the case that a syringe interface of the present invention is attachable to an injector, the syringe interface can be used as an adapter to attach a syringe to the injector that would otherwise be unusable with that injector.

In one aspect, the present invention provides a syringe interface for releasably attaching a syringe including a flange on a rearward end thereof to a front-loading injector including a reciprocating drive member or piston. The syringe interface includes a retaining member slideably positioned within a passage in the syringe interface to slide in a direction generally perpendicular to the orientation or to the axis of the piston to engage the syringe flange and retain the syringe within the syringe interface. The syringe interface can also include a rear portion including an attachment mechanism to attach the syringe interface to the injector (via, for example, a different type of syringe interface on the injector that cooperates with the attachment mechanism).

In another aspect, the present invention provides a syringe interface including a carriage slideably connected to the syringe interface in a direction generally parallel to the injector piston orientation. The carriage includes a seating member to engage the syringe flange. A forward portion of the syringe interface is rotatable relative to a rear portion of the syringe interface. The forward portion is adapted to engage the carriage upon rotation of the forward portion when the carriage is slid to a rearward position within the syringe interface. The syringe interface can also include a rear portion including an attachment mechanism to attach the adapter to an injector.

In another aspect, the present invention provides a syringe interface including a plurality of engagement members disposed around a passage in the syringe interface through which the injector piston passes. The syringe interface also includes a forward portion that is rotatable relative to the rear portion of the syringe interface. Rotation of the forward portion causes at least a portion of the engagement members to move radially inward to engage the syringe flange. The syringe interface can also include a rear portion having an attachment mechanism to attach the syringe interface to the injector.

In still another aspect, the present invention provides a syringe interface including a first retaining member slideably positioned within a first passage in the syringe interface to slide in a direction generally perpendicular to the orientation or to the axis of the injector piston. The syringe interface further includes a second retaining member slideably positioned within a second passage in the syringe interface to slide in a direction generally perpendicular to the orientation or to the axis of the piston. The orientation of the first retaining member generally opposes the orientation of the second retaining member. The first retaining member and the second retaining member are adapted to engage the syringe flange and retain the syringe within the adaptor when each is slid to a radially inward, closed position.

Preferably, the first retaining member and the second retaining member cooperate to engage the syringe flange around the entire perimeter of the syringe flange. The syringe interface can also include a rear portion including an attachment mechanism to attach the syringe interface to the injector.

In a further aspect, the present invention provides a syringe interface including a carriage slideably connected to the syringe interface in a direction generally parallel to the piston orientation or the axis of the piston. The carriage includes a seating member to engage a portion of the syringe flange. The syringe interface further includes a retaining member slideably positioned within a passage in the syringe interface to slide in a direction generally perpendicular to the orientation of the piston or to the axis of the piston when the syringe interface is attached to the injector. The carriage is slideable to a rearward position within the syringe interface at which the retaining member can be slid radially inward to engage another portion of the syringe flange and to retain the syringe within the adaptor. Preferably, the carriage and the retaining member cooperate to engage the syringe flange around the entire perimeter of the syringe flange. The syringe interface can further include a rear portion having an attachment mechanism to attach the syringe interface to the injector.

In still a further aspect, the present invention provides a syringe interface including a first retaining member that pivots about an axis generally offset from and perpendicular to the axis of the piston when the syringe interface is attached to the injector. The first retaining member pivots in a rearward direction to engage a portion of the syringe flange. The syringe interface further includes a second retaining member slideably positioned within a passage in the syringe interface to slide in a direction generally perpendicular to the axis of the piston to engage a portion of the syringe flange. The first retaining member and the second retaining member preferably cooperate to engage the syringe flange around the entire perimeter of the syringe flange. The first retaining member is preferably biased toward an open position. The syringe interface can also include a rear portion having an attachment mechanism to attach the syringe interface to the injector.

In still another aspect, the present invention provides a syringe interface for releasably attaching a syringe including a flange on a rearward end thereof to a front-loading injector including a reciprocating piston. The syringe interface includes a retaining member slideably positioned within a passage in the syringe interface to slide in a direction generally perpendicular to the axis of the piston to engage at least a portion of the syringe flange. The retaining member includes a plurality of abutment members in which adjacent abutment members are movably attached to each other. The abutment members follow a curved path when the retaining member is slid toward the axis of the piston (or radially inward) to form an abutment with at least a portion of the syringe flange. The syringe interface can also include a rear portion including an attachment mechanism to attach the syringe interface to the injector.

The present invention also provides injectors and injector systems including the syringe interfaces and adapters of the present invention, and methods for attaching syringes to the syringe interfaces and adapters.

BRIEF DESCRIPTION OF THE DRAWINGS

Other aspects of the invention and their advantages will be discerned from the following detailed description when read in connection with the accompanying drawings, in which:

FIG. 7F illustrates a perspective view of a portion of the syringe adapter of FIG. 7A in which the front plate or housing portion of the syringe adapter has been removed and in which the second retaining member is biased in an open position.

FIG. 10A illustrates a front, cross-sectional view of another embodiment of a syringe adapter of the present invention in an open state.

FIG. 10B illustrates a front, cross-sectional view of the syringe adapter of FIG. 10A in a closed state.

FIG. 10C illustrates a side, cross-sectional view of the syringe adapter of FIG. 10A in a closed state.

FIG. 11 illustrates a front, cross-sectional view of another embodiment of a syringe adapter of the present invention in an open state.

DETAILED DESCRIPTION OF THE INVENTION

Figure 1:
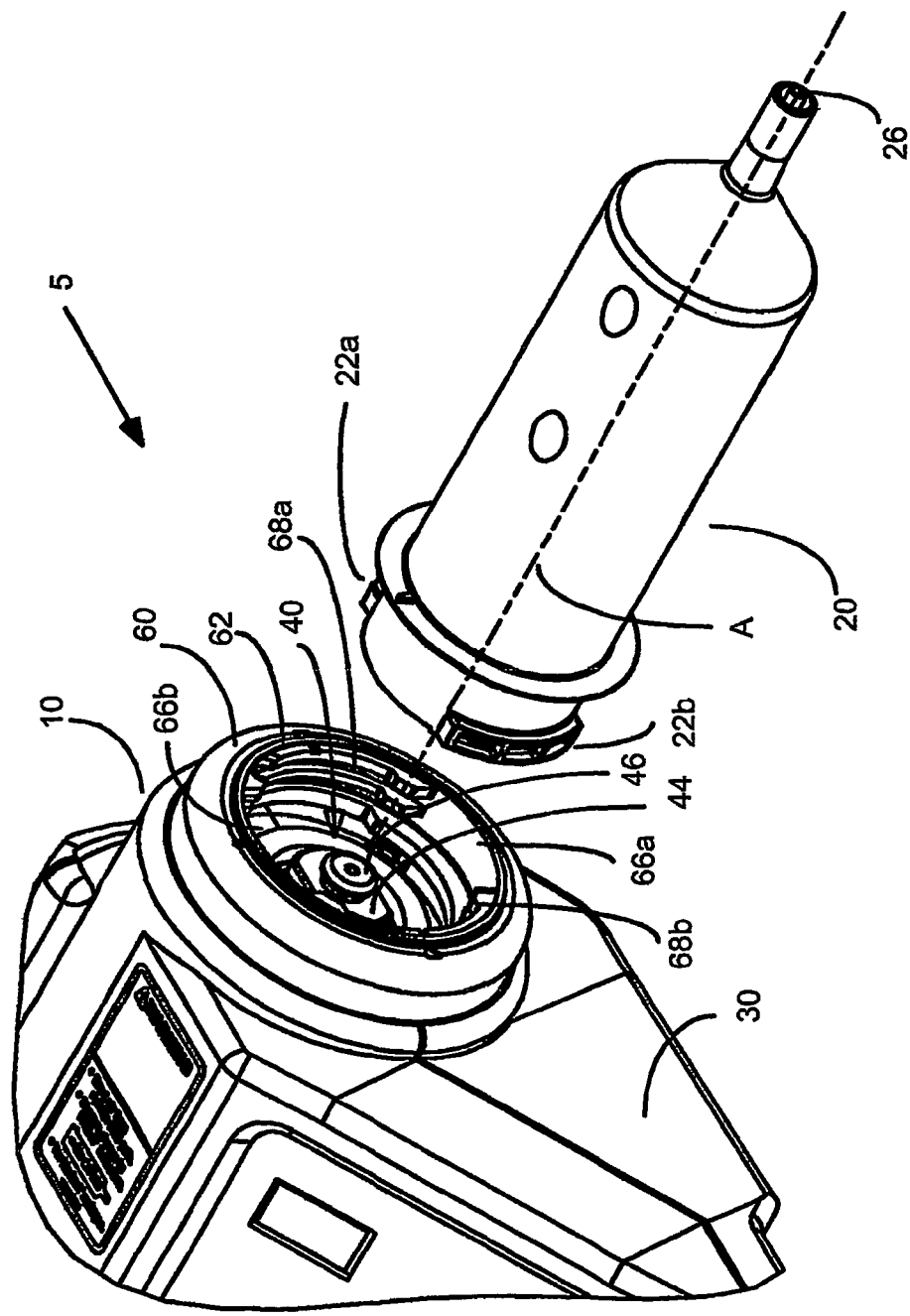
FIG. 1 illustrates a perspective view of an embodiment of an injector system including an injector and a front-loading syringe.

An embodiment of a front-loading injector system 5 of the present invention is illustrated in FIG. 1. Injector system 5 includes a powered injector 10 and a syringe 20 for injection of, for example, a contrast medium. An example of an injector 10 suitable for use in the present invention is the MEDRAD VISTRON CT® injector available from Medrad, Inc. of Indianola, Pa. However, the present invention may be used in connection with other fluid delivery systems, including injectors and infusion pumps for magnetic resonance imaging, computed tomography, ultrasound and angiographic procedures. As best illustrated in FIG. 1, injector housing 30 of injector 10 preferably includes a first drive member or piston 40 therein which cooperates with a syringe plunger (not shown in FIG. 1; see, for example, FIG. 7C) slideably disposed in syringe 20 to inject a fluid from the interior of syringe 20 into a patient.

As used herein to describe injection system 5 and other embodiments of the present invention, the terms "axial" or "axially" refer generally to, for example, an axis A around which syringe 20 and piston 40 are preferably formed (although not necessarily symmetrically therearound) and to directions collinear with or parallel to axis A. The terms "proximal" or "rearward" refer generally to an axial or a longitudinal direction toward the end of injector housing 30 opposite the end to which syringe 20 is mounted. The terms "distal" or "forward" refer generally to an axial or a longitudinal direction toward a syringe tip 26 of syringe 20 (from which pressurized fluid exits syringe 20). The term "radial" refers generally to a direction normal to an axis such as axis A.

Syringe 20 is preferably removably connected to injector 10 as described, for example, in U.S. Pat. No. 5,383,858, the disclosure of which is incorporated herein by reference. In that regard, front-loading injector 10 preferably includes a front portion or faceplate 60 having a first opening 62 formed therein. Piston 40 is reciprocally mounted within injector 10 and is extendible through opening 62. Piston 40 preferably includes a piston flange or head 44 to assist in forming a connection with the syringe plunger. Faceplate 60 includes receiving slots 66a and 66b, which are preferably positioned opposite one another around opening 62. Receiving flanges 68a and 68b are preferably positioned opposite one another and between receiving slots 66a and 66b and extend inwardly into opening 62.

The rearward end of syringe 20 preferably includes a mounting mechanism such as a pair of mounting flanges 22a and 22b for mounting syringe 20 in a desired position relative to the front wall 60 of injector 10. Flange 22b is not shown in FIG. 1 but is generally identical to flange 22a and positioned opposite flange 22a. Mounting flanges 22a and 22b may include one or more indicators (not shown), such as one or more detent(s), bar code(s), protrusion(s) or notch(es), which provide information to the injector 10, for example, about the type of syringe 20 and injection fluid being used. Correspondingly, injector 10 preferably includes any suitable detection mechanism (not shown) such as one or more sensors for reading information from the indicators.

To attach syringe 20 to injector 10, the rearward end of syringe 20 is inserted into injector opening 62 such that mounting flanges 22a and 22b are inserted into receiving slots 66a and 66b, respectively. Piston flange 44 preferably engages a capture mechanism on the rear of the syringe plunger (as, for example, described in U.S. Pat. No. 5,383,858).

Once mounting flanges 22a and 22b are inserted into receiving slots 66a and 66b, respectively, and piston 40 is in position to be received by the plunger, the operator rotates syringe 20 approximately 90 degrees such that mounting flanges 22a and 22b move behind and are engaged by receiving flanges 68a and 68b, respectively, and piston flange 44 is retained by, for example, L-shaped capture members on the plunger. Injector 10 may include a stop mechanism (not shown), for example, extending from at least one of the retaining slots 68a and 68b, to prevent rotation of syringe 20 more than 90 degrees. Tactile, visual or audible feedback can be provided to the operator via, for example, cooperating members on syringe 20 and injector 10 to inform the operator that a secure connection has been achieved. After securely attaching syringe 20 to injector 10, advancing piston 40 in a forward direction will apply a motive force to the plunger to advance the plunger forward within syringe 20, thereby forcing the contents of syringe 20 out of syringe tip 26 into the fluid path to the patient. Retracting piston 40 in a rearward direction will cause the plunger to move rearward within syringe 20, thereby drawing fluid into syringe 20.

Figure 2A:
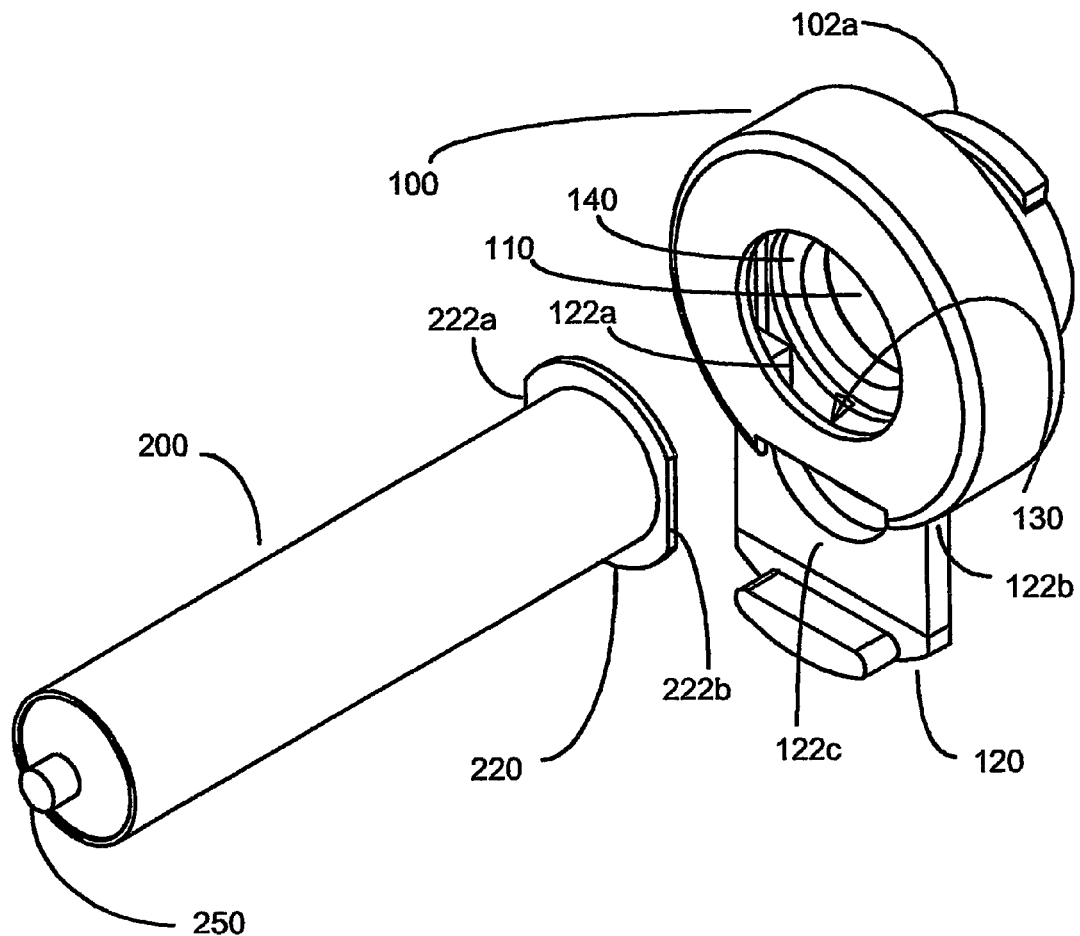
FIG. 2A illustrates a perspective view of an embodiment of a syringe and a syringe adapter for use with the injector of FIG. 1 in which the syringe and syringe adapter are in a disconnected state.
Figure 2B:
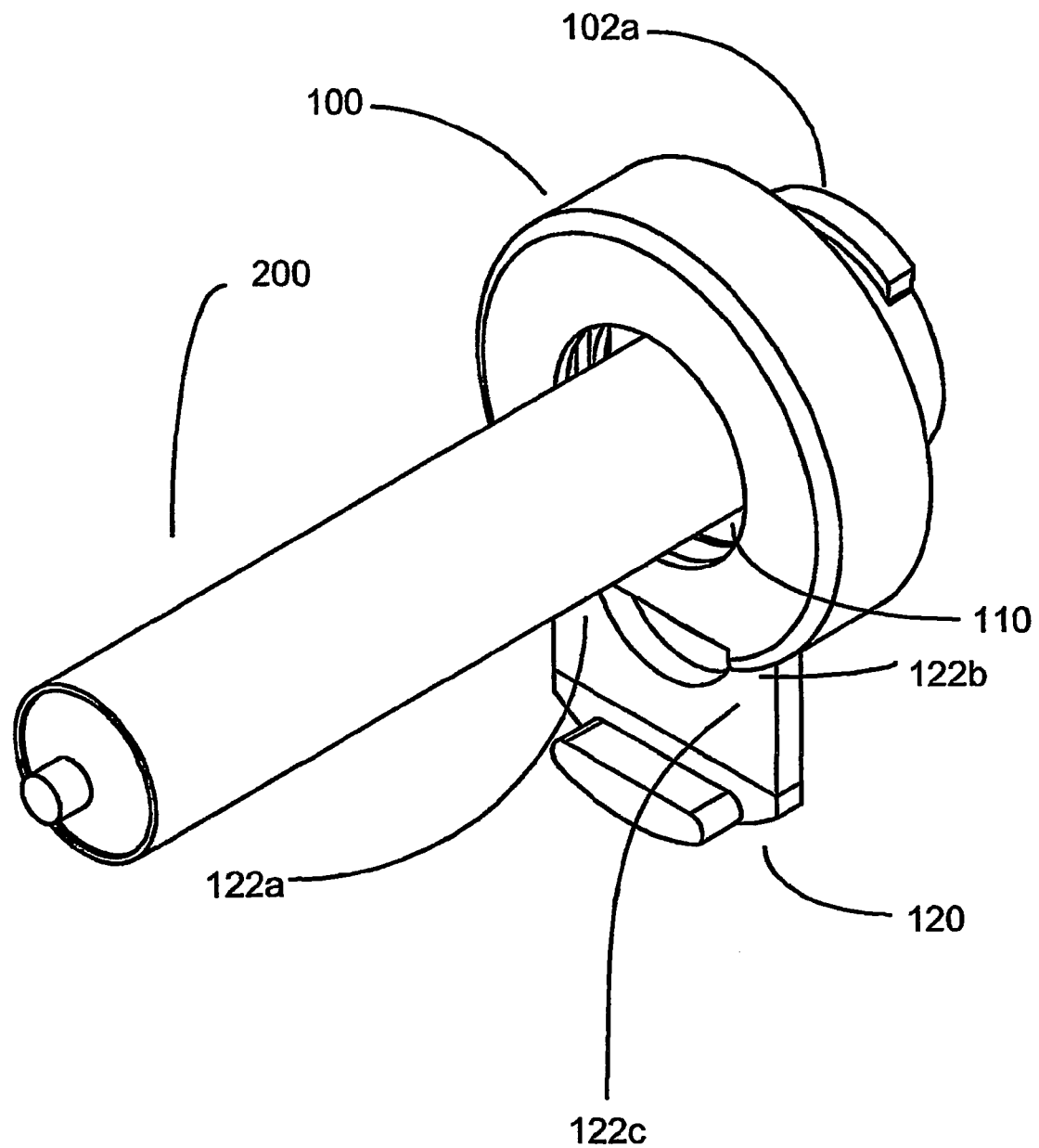
FIG. 2B illustrates a perspective view of the syringe and syringe adapter of FIG. 2A in which the syringe has been inserted into the syringe adapter.
Figure 2C:
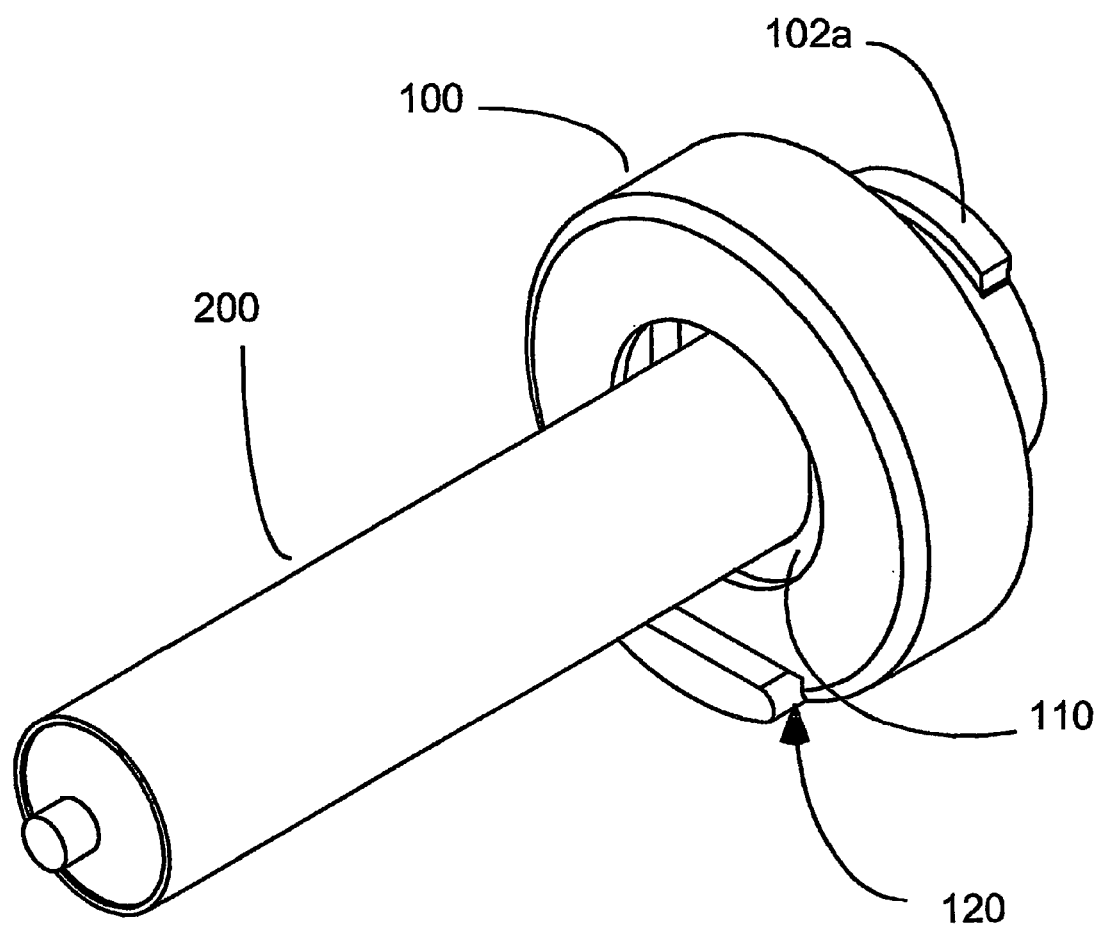
FIG. 2C illustrates a perspective view of the syringe and syringe adapter of FIG. 2A in which the syringe has been secured within the syringe adapter.

FIGS. 2A-2C illustrate one embodiment of a syringe interface/adapter 100 that is preferably attachable to injector 10 in a similar manner as described above for attachment of syringe 20 to injector 10. In that regard, a rearward portion or section of adapter 100 preferably includes a mounting mechanism such as a pair of mounting flanges 102a and 102b (not shown, but symmetrical to and positioned generally 180° opposite of mounting flange 102a) for mounting adapter 100 in a desired position relative to the front wall 60 of injector 10. Mounting flanges 102a and 102b may include indicators, such as detents or notches as described above, which provide information to injector 10 about the type of adapter and/or syringe being used.

To attach adapter 100 to injector 10, the rearward end of adapter 100 is inserted into injector opening 62 such that mounting flanges 102a and 102b are inserted into receiving slots 66a and 66b, respectively. Once mounting flanges 102a and 102b are inserted into receiving slots 66a and 66b, respectively, the operator preferably rotates adapter 100 approximately 90 degrees such that mounting flanges 102a and 102b move behind and are engaged by receiving flanges 68a and 68b, respectively. As described above, a stop mechanism (not shown) may, for example, extend from at least one of the retaining slots 68a and 68b, to prevent rotation of adapter 100 more than 90 degrees. Once again, tactile, visual or audible feedback can be provided to the operator via, for example, cooperating members on adapter 100 and injector 10 to inform the operator that a secure connection has been achieved.

Adapter 100 can, for example, be used to attach a syringe 200 including, for example, a rearward flange 220, to injector 10. In the embodiment of syringe 200, rearward flange 220 has a generally circular shape with straight or flattened, opposing sides 222a and 222b.

After securely attaching adapter 100 and syringe 200 to injector 10, advancing piston 40 in a forward direction applies a motive force to a plunger 210 (see, for example, FIG. 7C) within syringe 200 through passage 110 in adapter 100 to advance syringe plunger 210 forward within syringe 200, thereby forcing contrast medium in syringe 200 out of syringe tip 250 into the fluid path to the patient.

The attachment of syringe 200 to syringe interface/adapter 100 is illustrated in further detail in FIGS. 2A-2E. As illustrated in FIG. 2A, syringe 200 is first aligned with passage 110 in adapter 100. Preferably, it is not required that sides 222a and 222b of syringe 200 be in any particular alignment with adapter 100 or with the orientation of a sliding retaining member 120 slideably positioned within a passage 130 in adapter 100, thereby simplifying attachment. As illustrated in FIG. 2B, syringe 200 is then moved rearward until flange 220 is positioned to the rear of abutment members 122a and 122b. As discussed below in connection with FIGS. 8A through 8E, movement of syringe 200 to the rear can involve the attachment of a syringe plunger 210 to a plunger adapter 800 (see FIG. 8E) via, for example, rotating syringe 200 to thread syringe plunger 210 onto plunger adapter 800.

Once syringe 200 is in the position of FIG. 2B, retaining member 120 is slid upward or radially inward to a closed or secure position as illustrated in FIG. 2C. In this closed position, advancing piston 40 in a forward direction will cause the forward surface of syringe flange 220 to abut the rearward surfaces of abutment members 122a and 122b of retaining member 120 as well as the rearward surface of lower abutment member 122c (which connects abutment member 122a and 122b to form a generally U-shaped abutment member in retaining member 120), thereby retaining syringe 200 within adapter 100. Adapter 100 can also include a rear abutment surface 140 to assist in properly positioning syringe 200 within adapter 100. Should piston 40 be retracted, the rear surface of syringe flange 220 abuts rear abutment surface 140 to prevent syringe 200 from moving rearward within adapter 100.

Figure 3A:
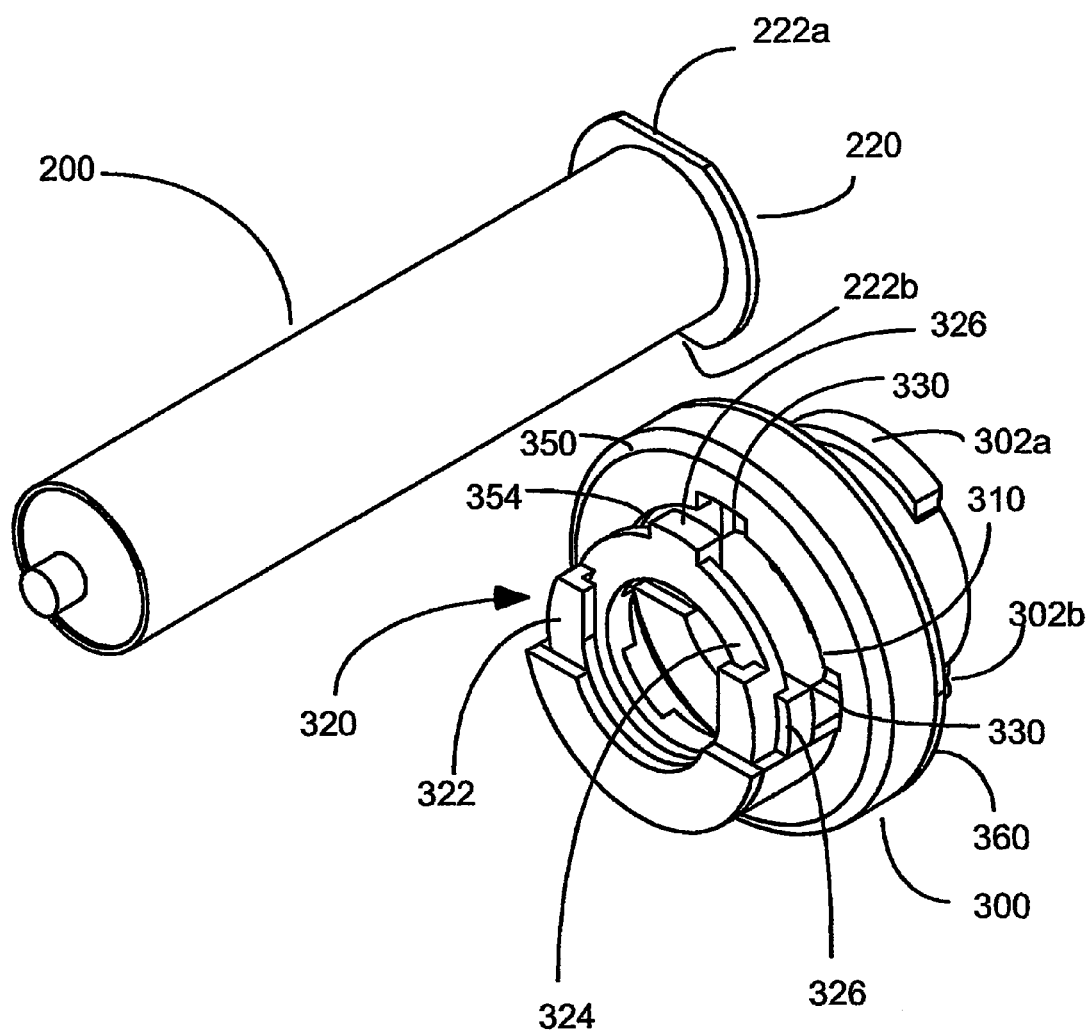
FIG. 3A illustrates a perspective view of another embodiment of a syringe and a syringe adapter for use with the injector of FIG. 1 in which the syringe and syringe adapter are in a disconnected state.
Figure 3B:
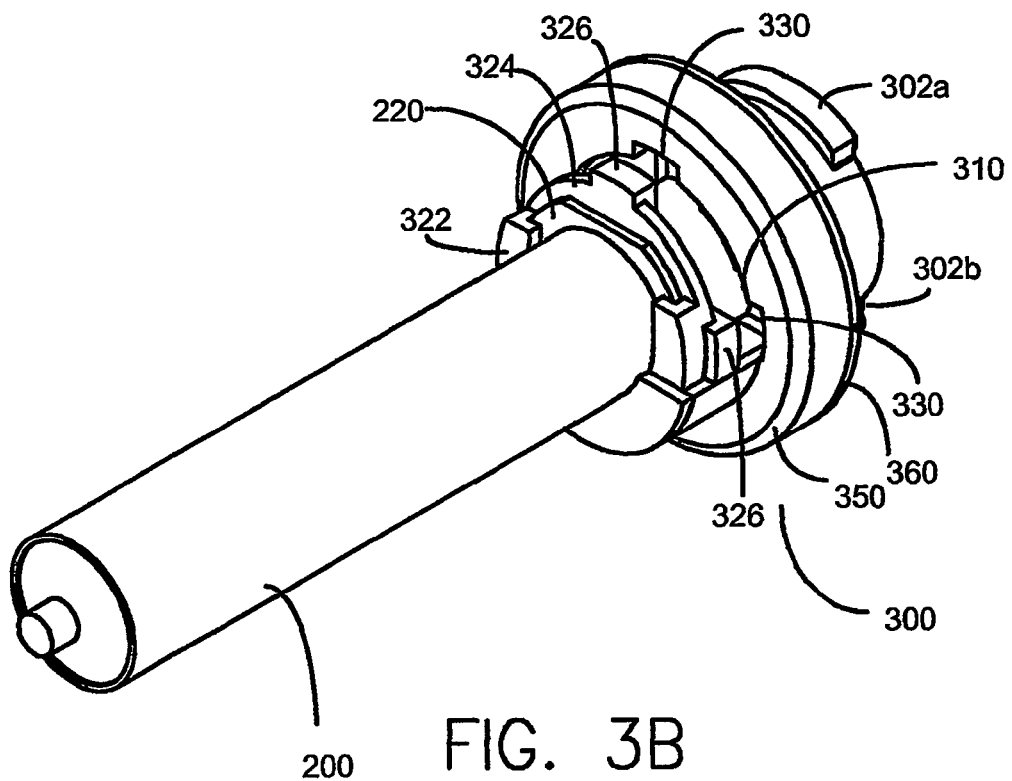
FIG. 3B illustrates a perspective view of the syringe and syringe adapter of FIG. 3A in which the syringe has been inserted into the syringe adapter carriage.

FIGS. 3A-3D illustrate another embodiment of an adapter 300 for connecting syringe 200 to injector 10. Adapter 300 includes a passage 310 within which a retaining carriage 320 is slideably disposed. As illustrated in FIG. 3A, syringe 200 is aligned with retaining carriage 320 such that flange 220 is generally aligned with an opening in the top of a generally U-shaped retention member 322 in retaining carriage 320. As illustrated in FIG. 3B, syringe 200 is then lowered so that syringe flange 220 seats between retention member 322 and a rear abutment surface 324 formed in retaining carriage 320. Preferably, it is not required that sides 222a and 222b of syringe flange 220 be in any particular alignment with respect the orientation of retention member 322. Indeed, in one aspect of the present invention, syringe 200 is preferably rotatable about its axis relative to adapter 300 when syringe flange 220 is seated within retention member 322 to, for example, allow syringe plunger 210 to be threaded onto plunger adapter 800 (see, for example, FIG. 8E).

Figure 3C:
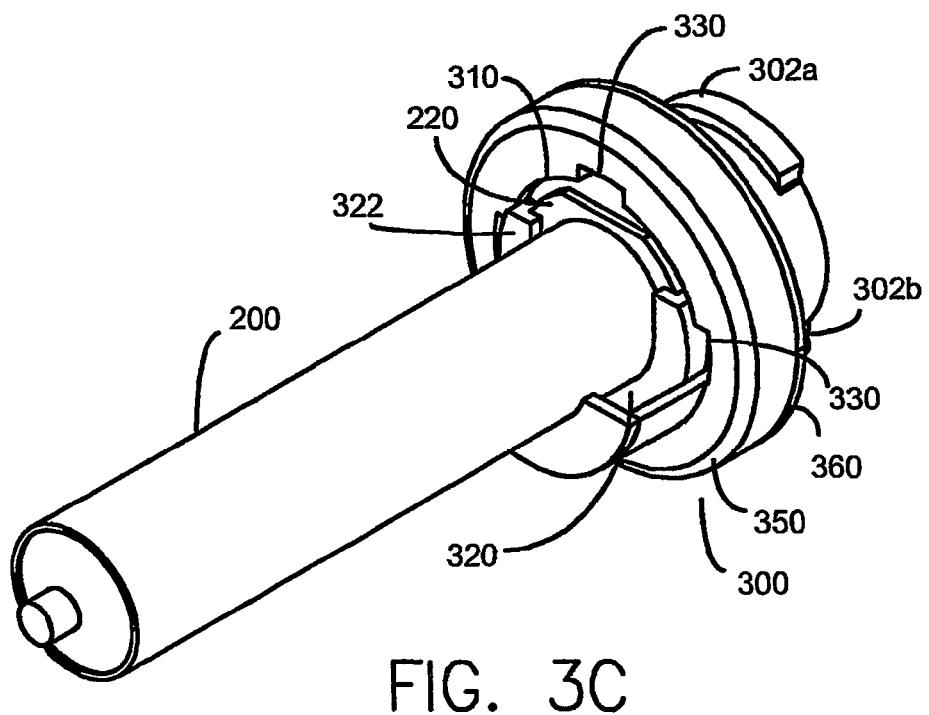
FIG. 3C illustrates a perspective view of the syringe and syringe adapter of FIG. 3A in which the syringe has been moved rearward within the syringe adapter.
Figure 3D:
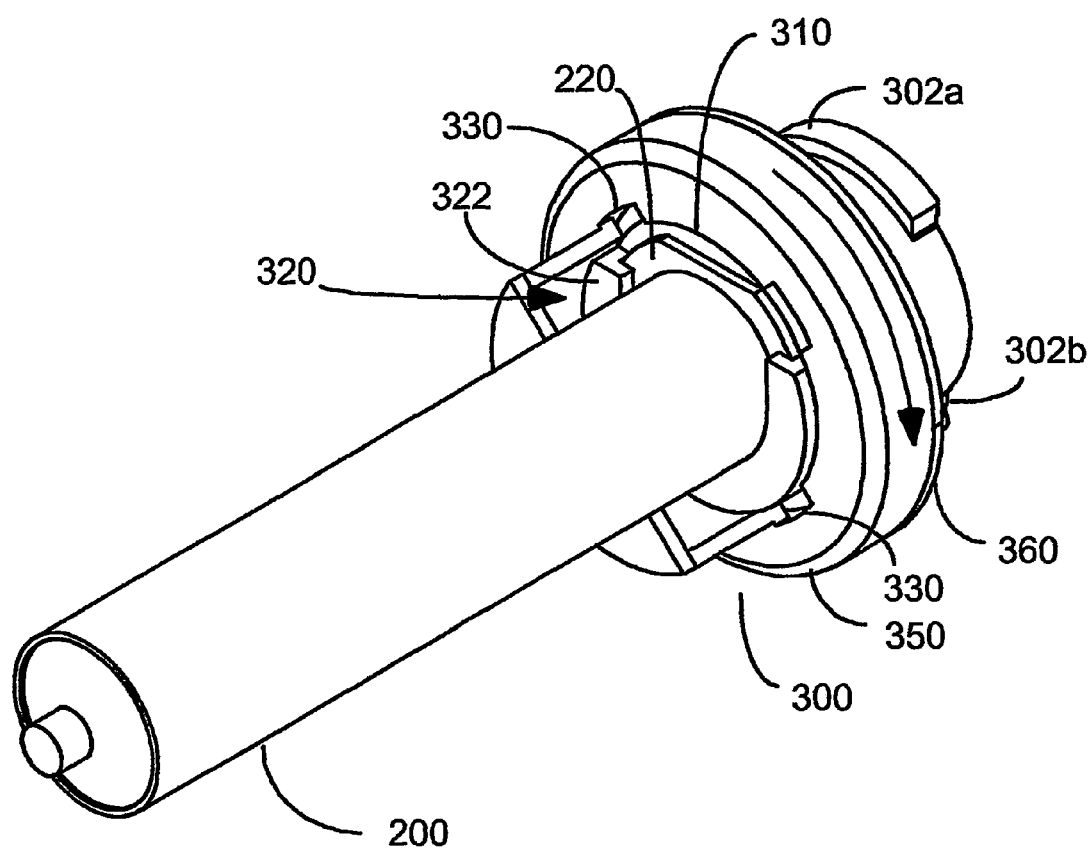
FIG. 3D illustrates a perspective view of the syringe and syringe adapter of FIG. 3A in which the syringe adapter has been rotated to secure the syringe within the syringe adapter.

After syringe 200 is seated within retaining carriage 320, retaining carriage 320 is slid rearward within passage 310 of adapter 300 as illustrated in FIG. 3C. As discussed above, in some embodiments, syringe 200 can be rotated during such rearward movement to connect syringe plunger 210 to plunger adapter 800. In the embodiment of FIGS. 3A-3D, carriage 320 includes tabs 326 that pass through corresponding keyways 330 formed around passage 310. Once retaining carriage 320 is slid rearward within adapter 300, front portion or wall 350 of adapter 300 is rotated relative to the rear portion 360 of adapter 300 (to which mounting flanges 302a and 302b are connected) as represented by the arrow in FIG. 3D. When face portion 350 is rotated relative to the remainder of adapter 300, tabs 326 become positioned behind a carriage retaining flange 354 (see, for example, FIG. 3A) formed by the face portion 350 of adapter 300. When piston 40 is advanced, retaining carriage 320 is prevented from sliding forward within adapter 300 by the abutment of the forward surfaces of tabs 326 with the rearward surface of carriage retaining flange 354. Syringe 200 is retained within adapter 300 by the abutment of the forward surface of syringe flange 220 with a rearward-facing surface of retention member 322.

Figure 4A:
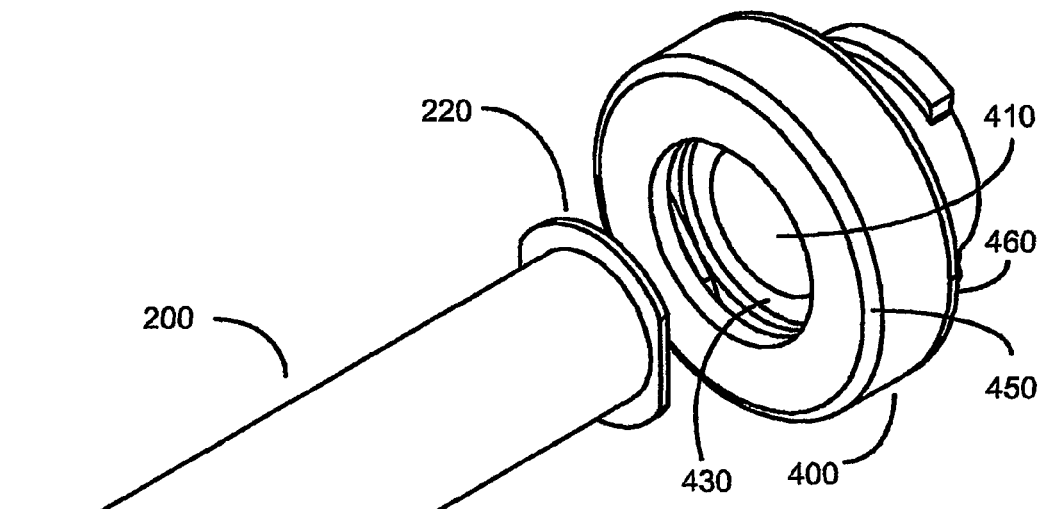
FIG. 4A illustrates a perspective view of another embodiment of a syringe and a syringe adapter for use with the injector of FIG. 1 in which the syringe and syringe adapter are in a disconnected state.
Figure 4B:
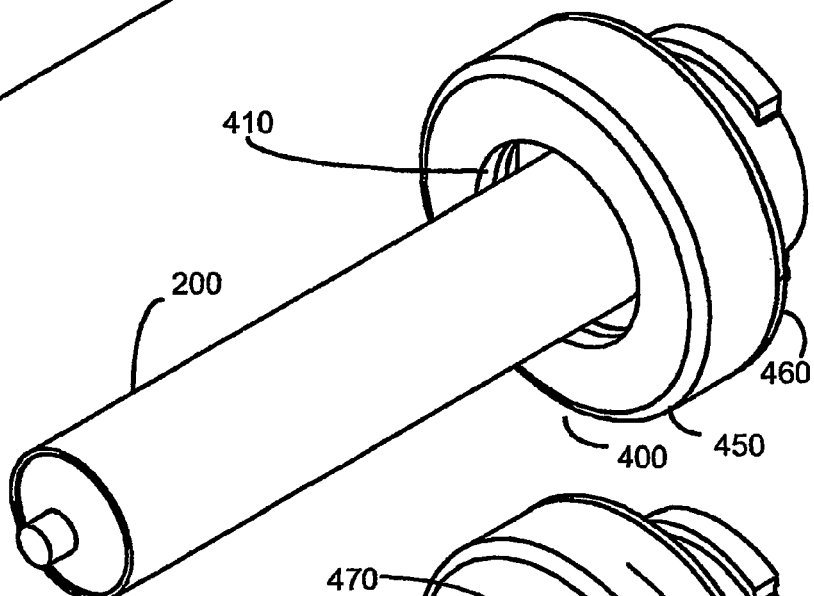
FIG. 4B illustrates a perspective view of the syringe and syringe adapter of FIG. 4A in which the syringe has been inserted into the syringe adapter.
Figure 4D:
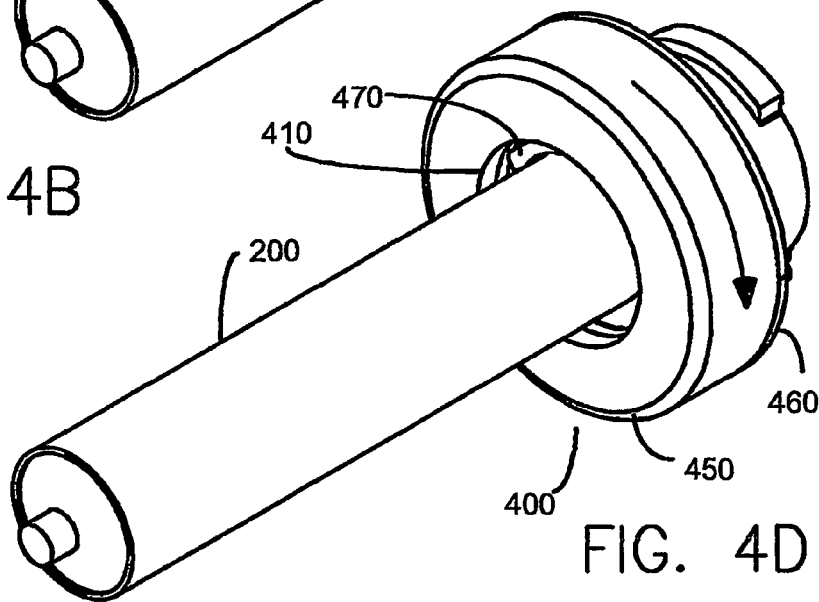
FIG. 4D illustrates a perspective view of the syringe and syringe adapter of FIG. 4A in which the front portion of the adapter has been rotated relative to the rear portion of the adapter to cause retaining arms of the adapter to engage and secure the syringe within the adapter.
Figure 4C:
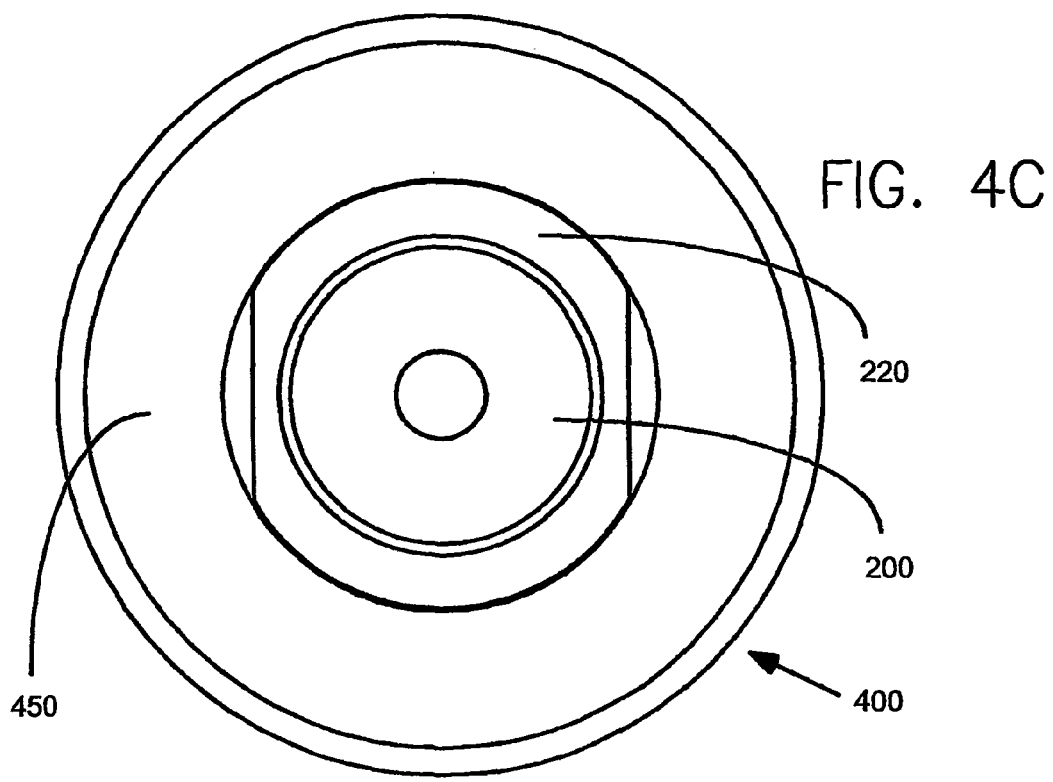
FIG. 4C illustrates a front view of the syringe and syringe adapter of FIG. 4A in the position of FIG. 4B.
Figure 4E:
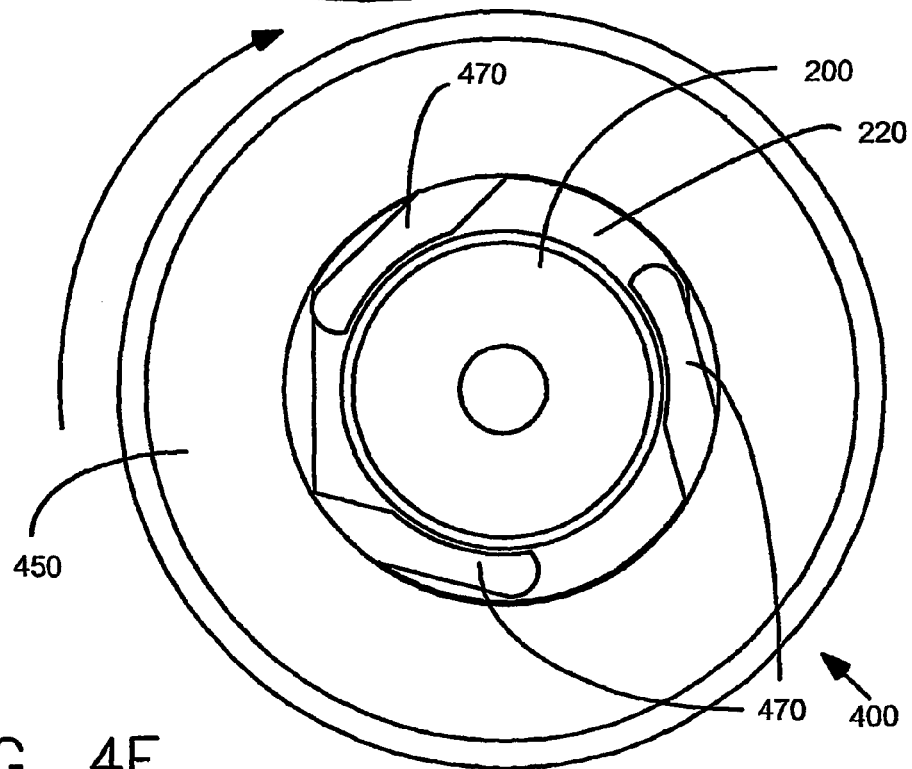
FIG. 4E illustrates a front view of the syringe and syringe adapter of FIG. 4A in the position of FIG. 4D.

FIGS. 4A-4E illustrate another embodiment of an adapter 400 for connecting syringe 200 to injector 10. As illustrated in FIGS. 4A and 4B, syringe 200 is first aligned with passage 410 in adapter 400 and then moved rearward into adapter 400. Adapter 400 can, for example, include a rear abutment surface 430 to assist in properly positioning syringe 200 within adapter 400. After syringe 200 is inserted within adapter 400 as illustrated in FIGS. 4B and 4C (which can in some embodiments include rotation of syringe plunger 210 onto plunger adapter 800 as discussed above), a front or face portion 450 of adapter 400 is rotated relative to a rear portion 460 thereof as illustrated in FIGS. 4D and 4E. Rotation of face portion 450 causes engagement arms 470 to move inward toward the center of adapter 400.

Figure 4F:
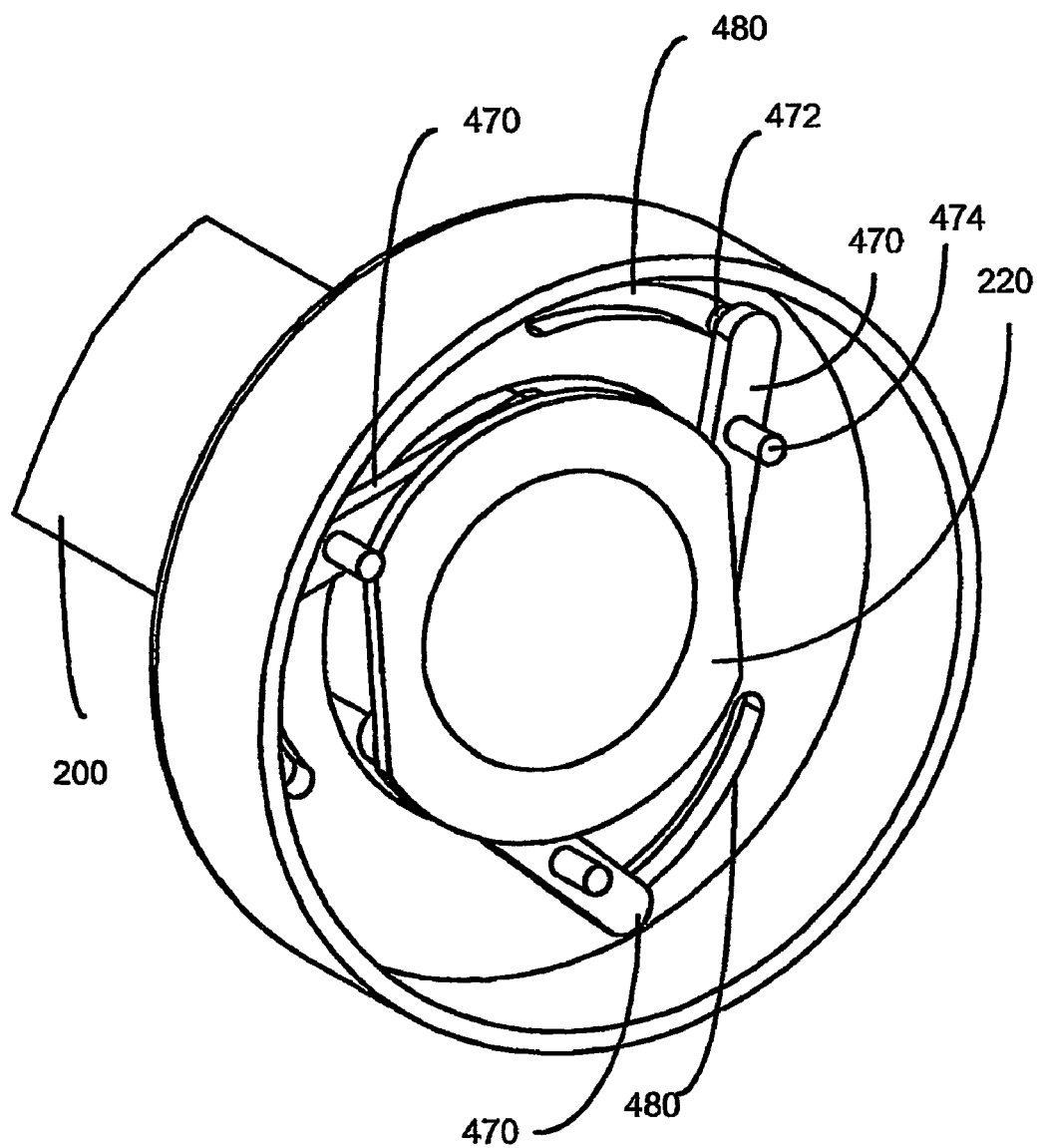
FIG. 4F illustrates a rear, perspective view of the syringe and syringe adapter of FIG. 4A in which the front portion of the adapter has been rotated relative to the rear portion of the adapter to cause retaining arms of the adapter to engage and secure the syringe within the adapter.

In one embodiment, as illustrated in FIG. 4F, rotation of front portion 450 of adapter 400, causes pins or extensions 472 on a radially outer portion of each engagement arm 470 to move along eccentric oriented grooves 480 formed in front portion 450, thereby causing engagement arms 470 to rotate about a pivot point 474, and thereby causing a radially inner portion of engagement arms 470 to move inward toward the center of adapter 400 to contact syringe flange 220. The rearward surface of engagement arms 470 contacts the forward surface of syringe flange 220 to retain syringe 200 within adapter 400. As illustrated in FIG. 4E, the radially inward portions of engagement arms 470 can be contoured to mate with the generally cylindrical shape of syringe 200.

Preferably, engagement arms 470 are positioned around the axis of adapter 400 such that the contact of engagement arms 470 with flange 220 is generally symmetrical about the axis of syringe 200. Such symmetrical contact about the axis of syringe 200 reduces or prevents bending moments upon syringe 200 when piston 40 is advanced.

Figure 5A:
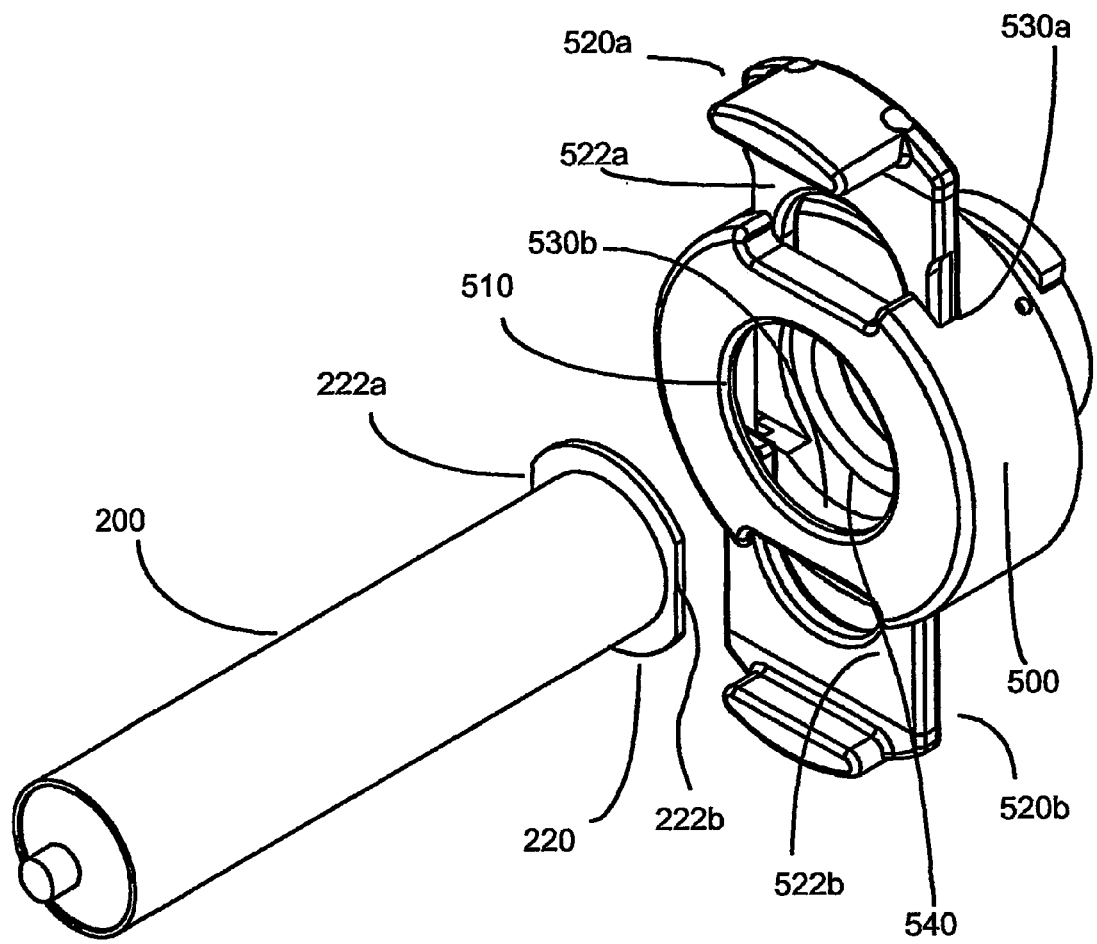
FIG. 5A illustrates a perspective view of another embodiment of a syringe and a syringe adapter for use with the injector of FIG. 1 in which the syringe and syringe adapter are in a disconnected state.
Figure 5B:
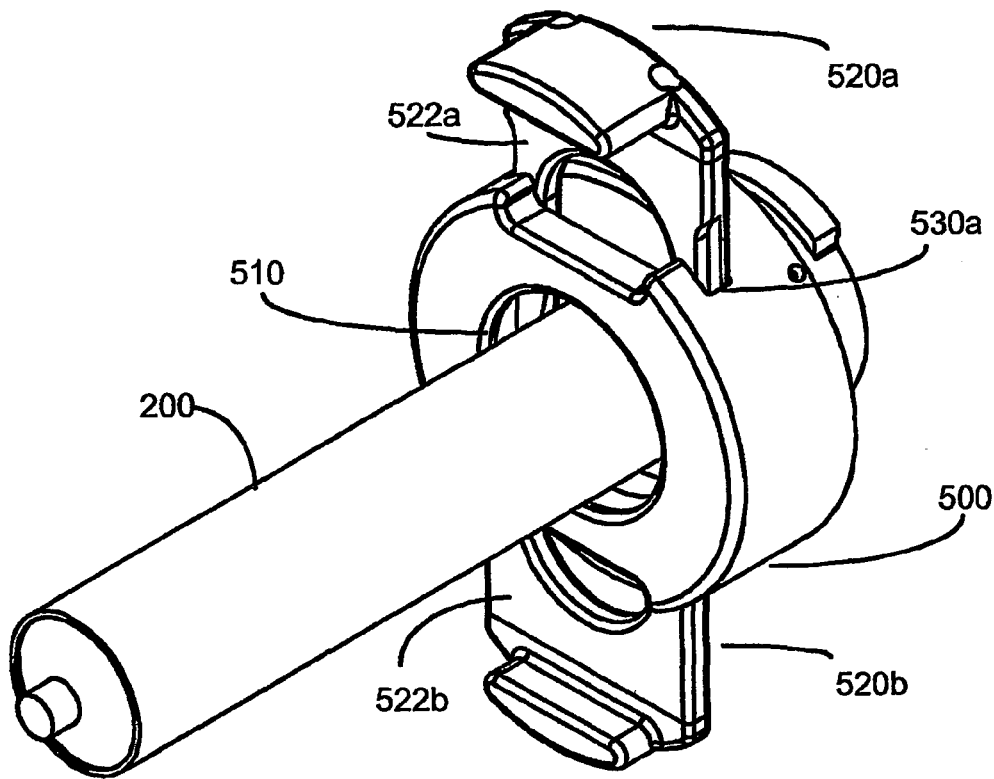
FIG. 5B illustrates a perspective view of the syringe and syringe adapter of FIG. 5A in which the syringe has been inserted into the syringe adapter.
Figure 5C:
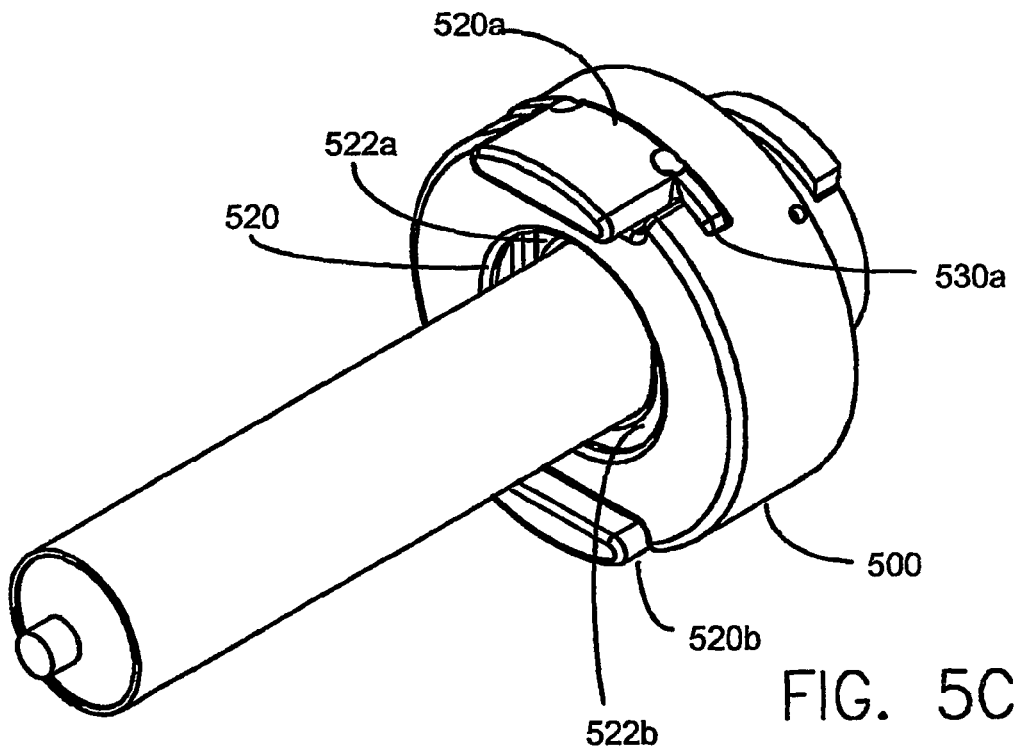
FIG. 5C illustrates a perspective view of the syringe and syringe adapter of FIG. 5A in which the syringe has been secured within the syringe adapter.

Another embodiment of an adapter 500 of the present invention is illustrated in FIGS. 5A-5C. Adapter 500 is similar in operation to adapter 100. However, adapter 500 includes two, generally opposing sliding retaining members 520a and 520b. As illustrated in FIG. 5A, syringe 200 is first aligned with passage 510 in adapter 500. Preferably, no specific orientation of generally flat sides 222a and 222b of syringe flange 220 is required with respect to the orientation of sliding retaining members 520a and 520b, which are slideably positioned within passages 530a and 530b in adapter 500.

As illustrated in FIG. 5B, syringe 200 is moved rearward until flange 220 is positioned to the rear of U-shaped abutment members 522a and 522b of sliding retaining members 520a and 520b, respectively. As discussed above, rearward movement of syringe 200 can include attachment (for example, by rotation relative thereto) of syringe plunger 210 to plunger adapter 800. Once syringe 200 is in the position of FIG. 5B, retaining members 520a and 520b are slid radially inward to a closed or secure position as illustrated in FIG. 5C. In this closed position, advancing piston 40 in a forward direction causes the forward surface of syringe flange 220 to abut the rearward surfaces of U-shaped abutment members 522a and 522b of retaining members 520a and 520b, respectively, thereby retaining syringe 200 within adapter 500. Adapter 500 can also include a rear abutment surface 540.

Unlike the case of adapter 100 and the other adapters described above, the two sliding retaining members 520a and 520b of adapter 500 fully engage or encompass rear flange 220 of syringe 200 (that is, U-shaped abutment members 522a and 522b contact the forward surface of flange 220 around the entire perimeter of flange 220). Because the contact is symmetrical about the axis of syringe 200, advancing piston 40 does not result in bending moments upon syringe 200, as described above for adapter 400. Moreover, full contact around the perimeter of syringe flange 220 by adapter 500 distributes forces over the entirety of syringe flange 220 and thus enables syringe flange 220 to endure greater force without distortion or failure as compared to the case in which only part of flange 220 is contacted by a retaining or abutment member. Furthermore, fill contact with syringe flange 220 enables manufacture of syringe 200 from materials that might fail under conditions of only partial contact of a retaining member with syringe flange 220.

FIGS. 6A-6D illustrate another embodiment of an adapter 600 including a sliding retaining member 620 having a generally U-shaped abutment member 622 that operates in generally the same manner as sliding retaining member 520a described above. Adapter 600 also includes a retaining carriage 630 that is generally axially slideable within passage 610 of adapter 600 via passages 632 (see FIGS. 6C and 6D) that cooperate with or slide upon guide rails 634. End member 636 prevents carriage 630 from being removed from guide rails 634. Retaining carriage 630 also includes a generally U-shaped abutment member 638 (similar to retention or abutment member 322 of adapter 300) in which syringe flange 220 is preferably seated (and, in some embodiments, as discussed above in connection with retention member 322, rotatably (about its axis) seated).

Figure 6A:
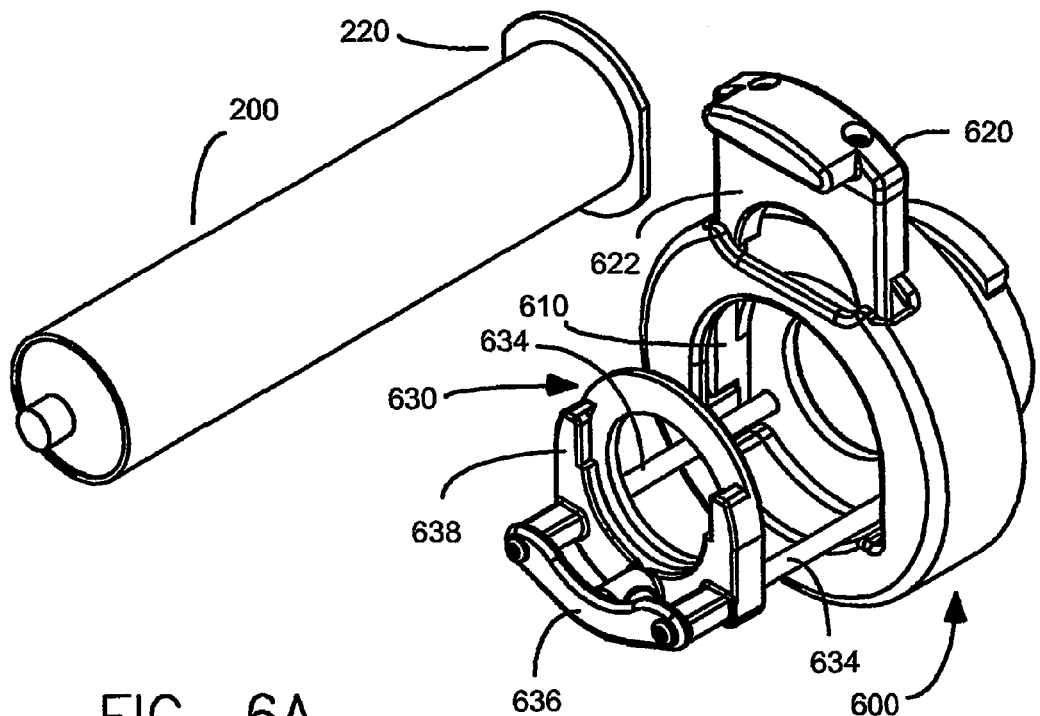
FIG. 6A illustrates a perspective view of another embodiment of a syringe and a syringe adapter for use with the injector of FIG. 1 in which the syringe and syringe adapter are in a disconnected state.
Figure 6B:
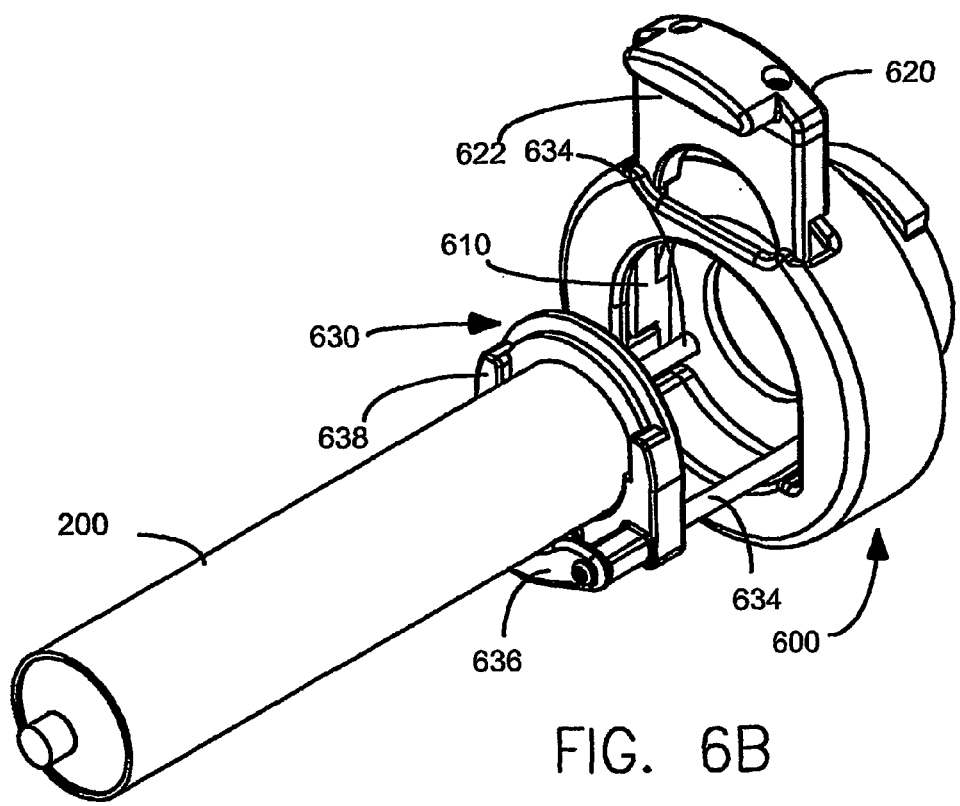
FIG. 6B illustrates a perspective view of the syringe and syringe adapter of FIG. 6A in which the syringe has been inserted into carriage of the syringe adapter.
Figure 6C:
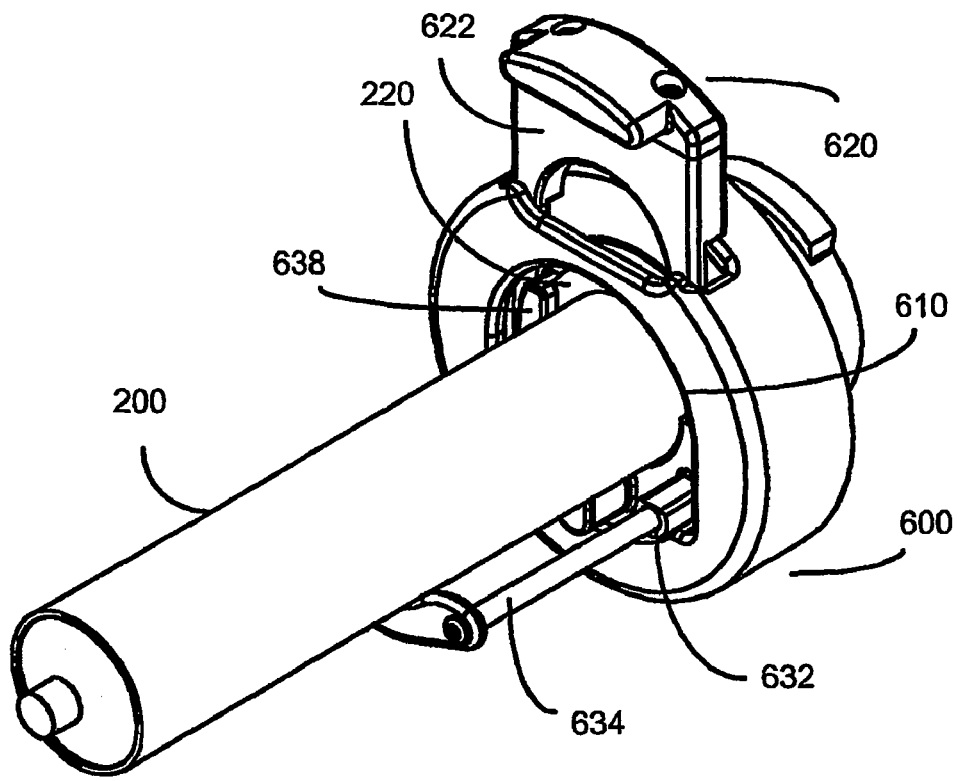
FIG. 6C illustrates a perspective view of the syringe and syringe adapter of FIG. 6A in which the syringe and carriage have been slid rearward within the syringe adapter.
Figure 6D:
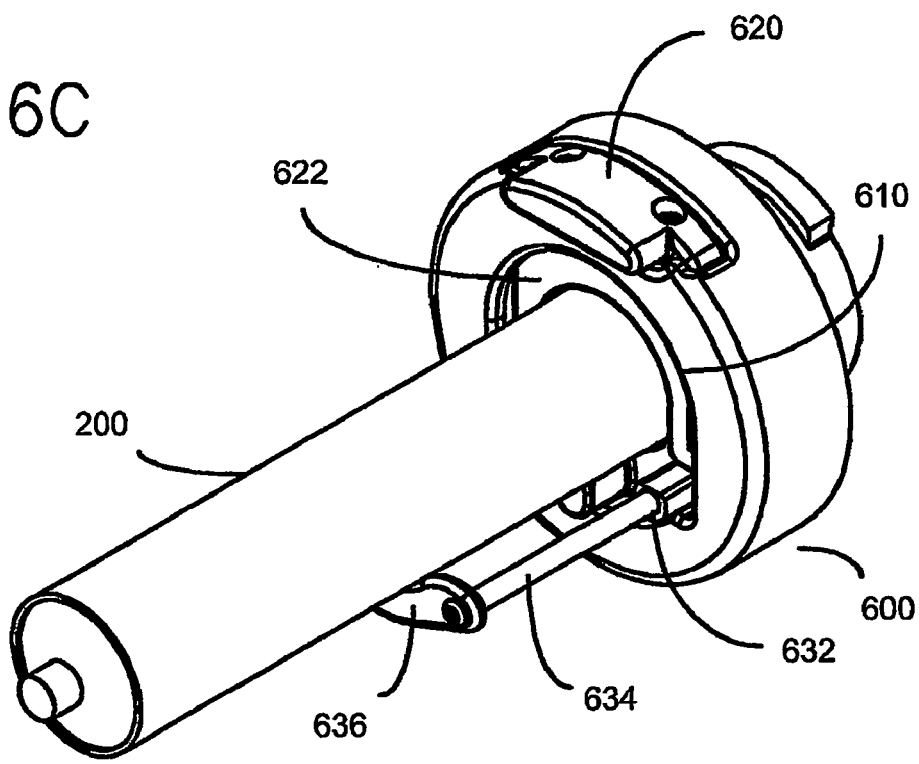
FIG. 6D illustrates a perspective view of the syringe and syringe adapter of FIG. 6A in which the retaining member has been slid radially inward to secure the syringe within the syringe adapter.

As illustrated in FIG. 6B, a syringe 200 is seated within retention or abutment member 638 of carriage 630. Carriage 630 is then slid rearward within adapter 600 to the position illustrated in FIG. 6C. In this position, abutment member 622 of retaining member 620 is in general alignment with syringe flange 220 and abutment member 638 so that retaining member 620 can be slid radially inward to engage flange 220 with abutment member 622 as illustrated in FIG. 6D. Similar to the case of adapter 500, abutment member 622 and abutment member 638 symmetrically and fully encompass or engage syringe flange 220 when in the closed or secured position of FIG. 6D. Sliding retaining member 620 and carriage 630 can, for example, interlock to secure the adapter in a closed position.

FIGS. 7A-7G illustrate an embodiment of an adapter 700 that includes a sliding retaining member 720 having a generally U-shaped abutment member or retention member 722 that operates in a similar manner as described above for sliding retention member 622. Adapter 700 also includes a second retaining member 730 that pivots about an axis A' radially offset from, and oriented generally perpendicular to, axis A" of syringe 200 and adapter 700.

Figure 7A:
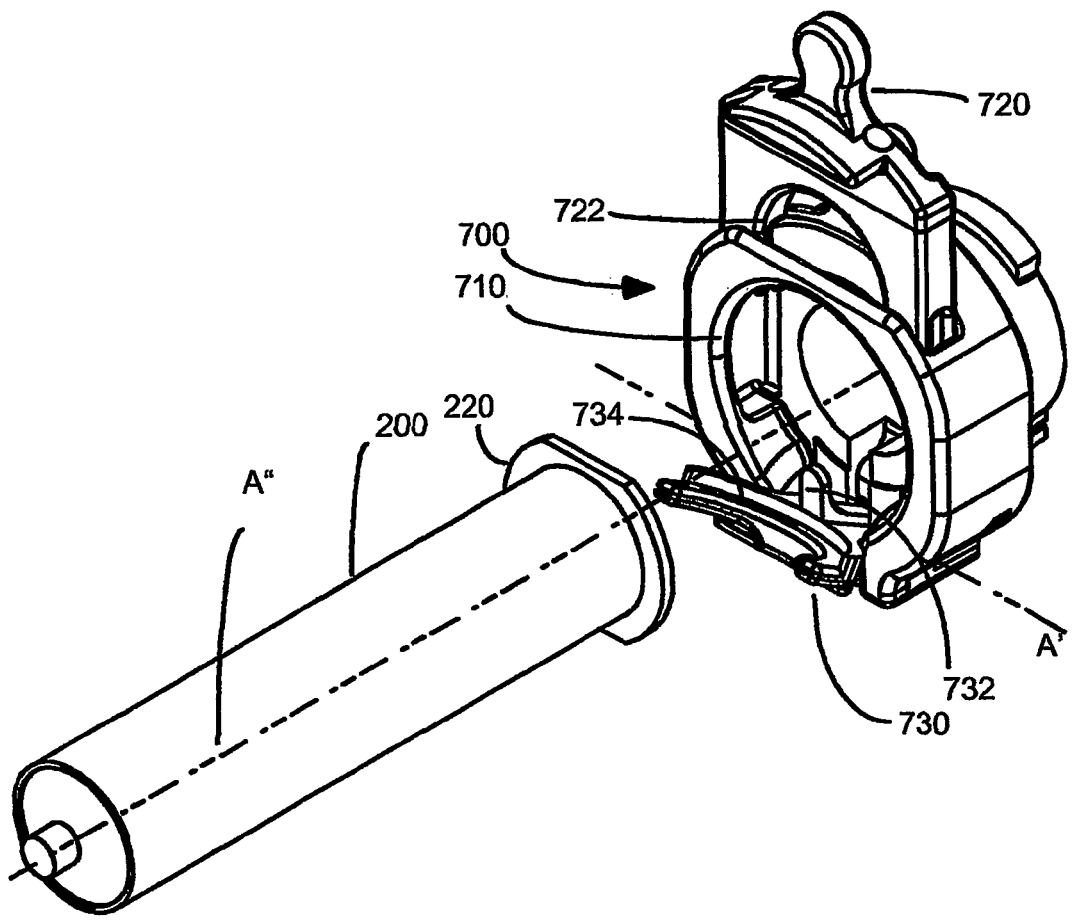
FIG. 7A illustrates a perspective view of another embodiment of a syringe and a syringe adapter for use with the injector of FIG. 1 in which the syringe and syringe adapter are in a disconnected state.
Figure 7B:
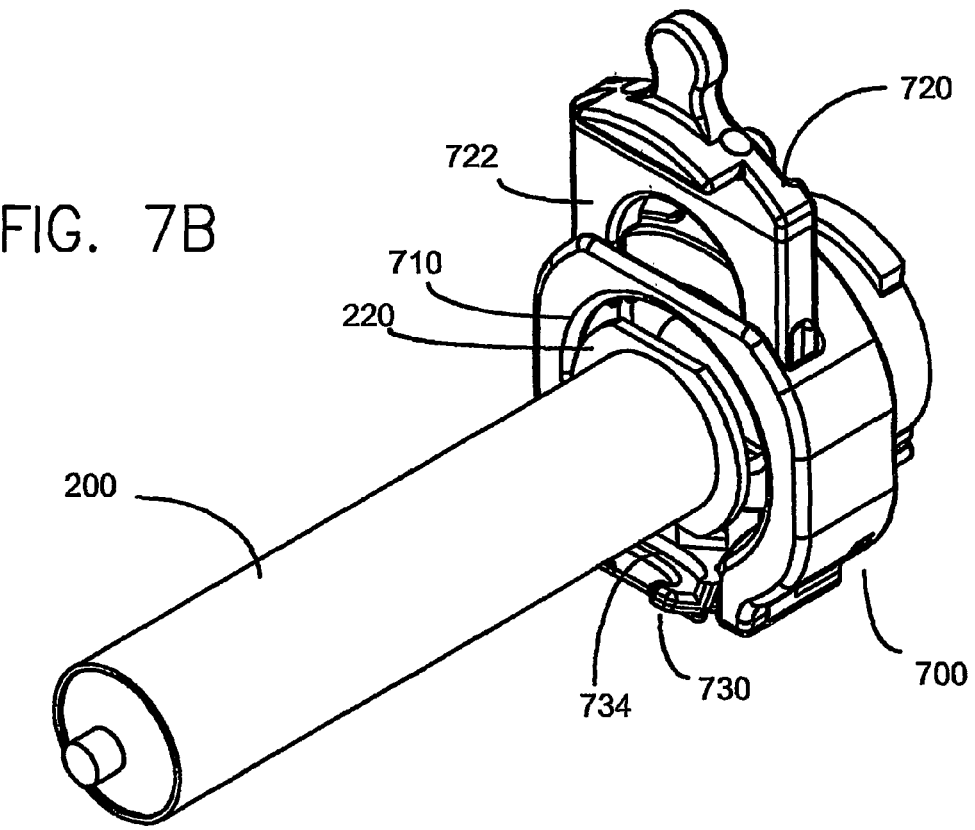
FIG. 7B illustrates a perspective view of the syringe and syringe adapter of FIG. 7A in which the syringe has engaged a pivoting, second retaining member of the syringe adapter.
Figure 7C:
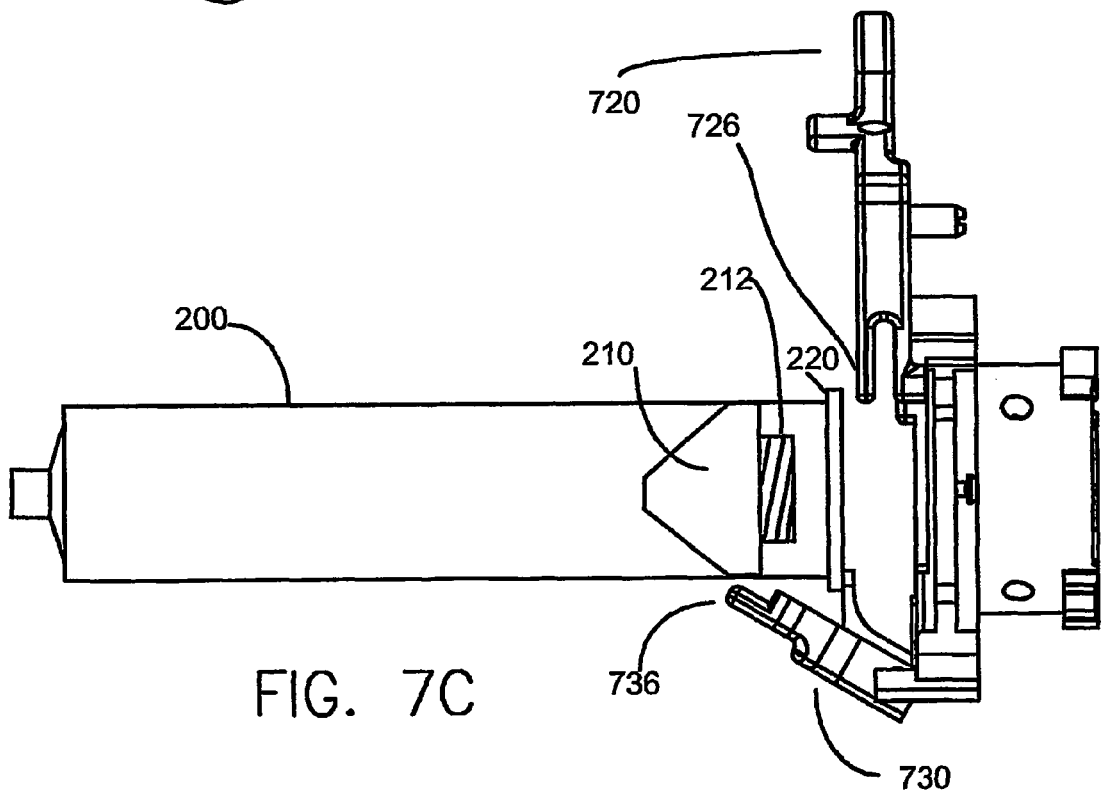
FIG. 7C illustrates a side view of the syringe and syringe adapter of FIG. 7A in the position of FIG. 7B in which the faceplate or front portion of the adapter has been removed.
Figure 7D:
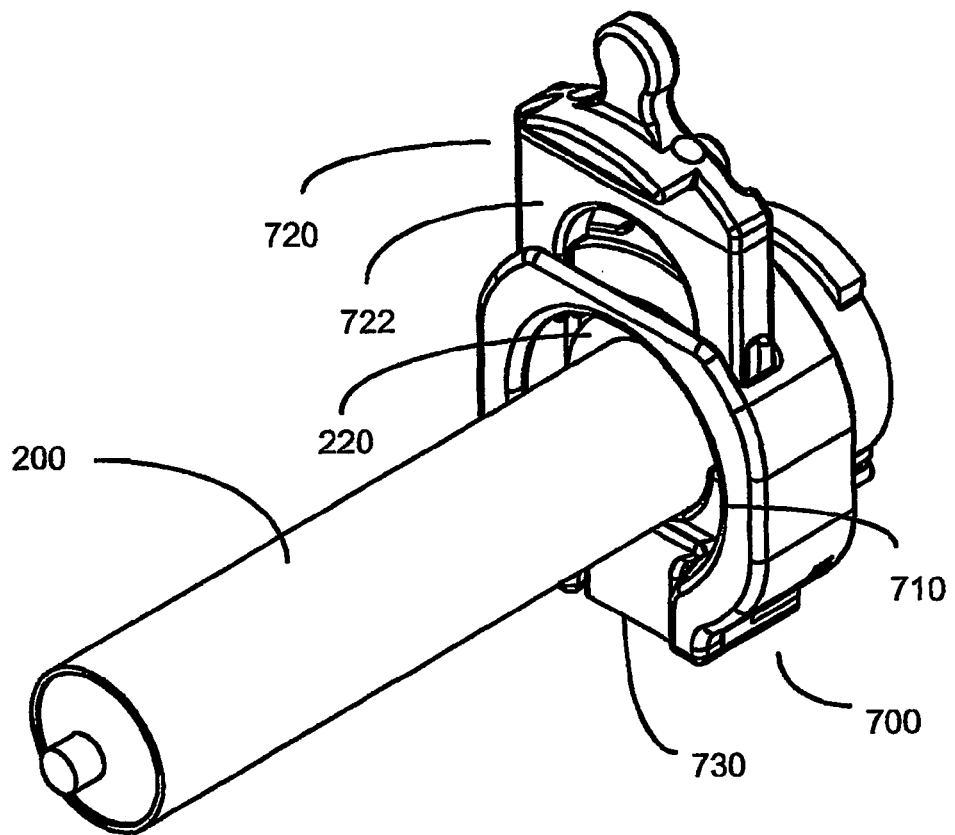
FIG. 7D illustrates a perspective view of the syringe and syringe adapter of FIG. 7A in which the syringe has been moved rearward to be secured by the second retaining member.
Figure 7E:
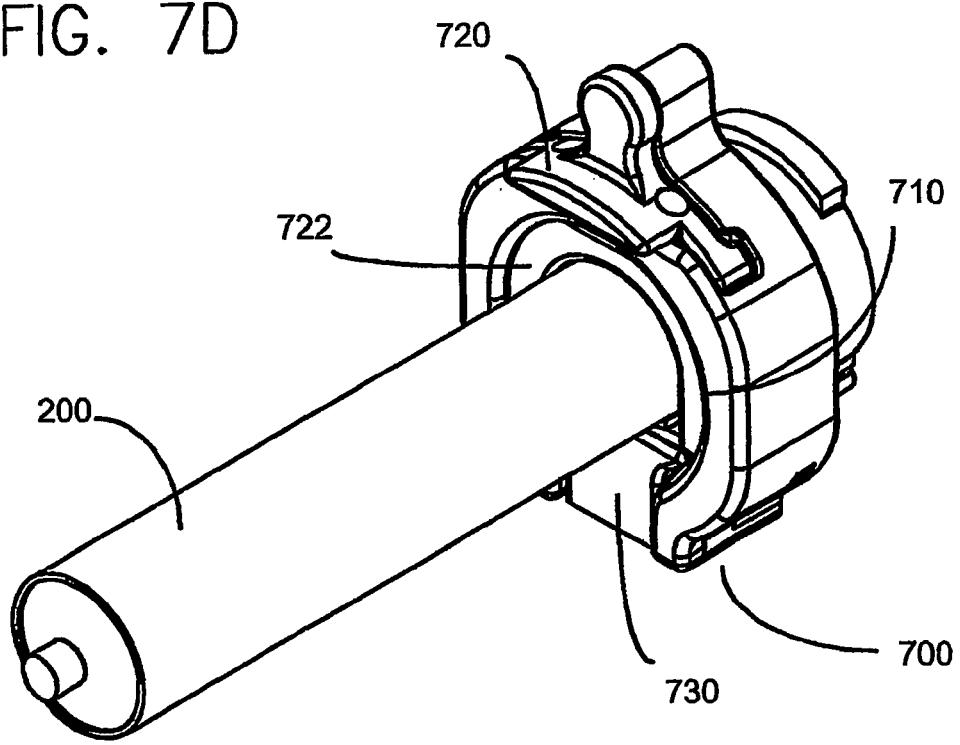
FIG. 7E illustrates a perspective view of the syringe and syringe adapter of FIG. 7A in which the sliding retaining member has been placed in a closed position to secure the syringe within the syringe adapter.

As illustrated in FIG. 7A, syringe 200 is preferably aligned with passage 710 in adapter 700. Syringe 200 is then moved rearward so that the rear surface of syringe flange 220 contacts a contact member 732 of second retaining member 730 as illustrated in FIGS. 7B, 7C and 7F. Contact of flange 220 with contact member 732 and further rearward movement of syringe 200 (which can include rotation of syringe 200 about its axis relative to plunger adapter 800 as discussed above) causes second retaining member 730 to pivot or rock rearward about axis A' so that second retaining member 730 becomes generally vertically oriented (generally perpendicular to axis A") and generally in plane with retaining member 720. This position of syringe 200 within adapter 700 is shown in FIG. 7D.

In this position, abutment surface 734 of second retaining member 730 comes into contact with the forward surface of flange 220. At this point, retaining member 720 is slid radially inward (or downward in the orientation of FIGS. 7A through 7G) to interlock with second retaining member 730 (via, for example, interlocking extending members 726 and 736) to secure syringe 200 within adapter 700. Retaining members 720 and 730 symmetrically and fully encompass syringe flange 220.

Adapter 700 enables the removal of syringe 200 from adapter 700 without the rearward retraction of piston 40. In that regard, first retaining member 720 can be slid radially outward and second retaining member 730 pivoted forward to fully release syringe 200.

Figure 7G:
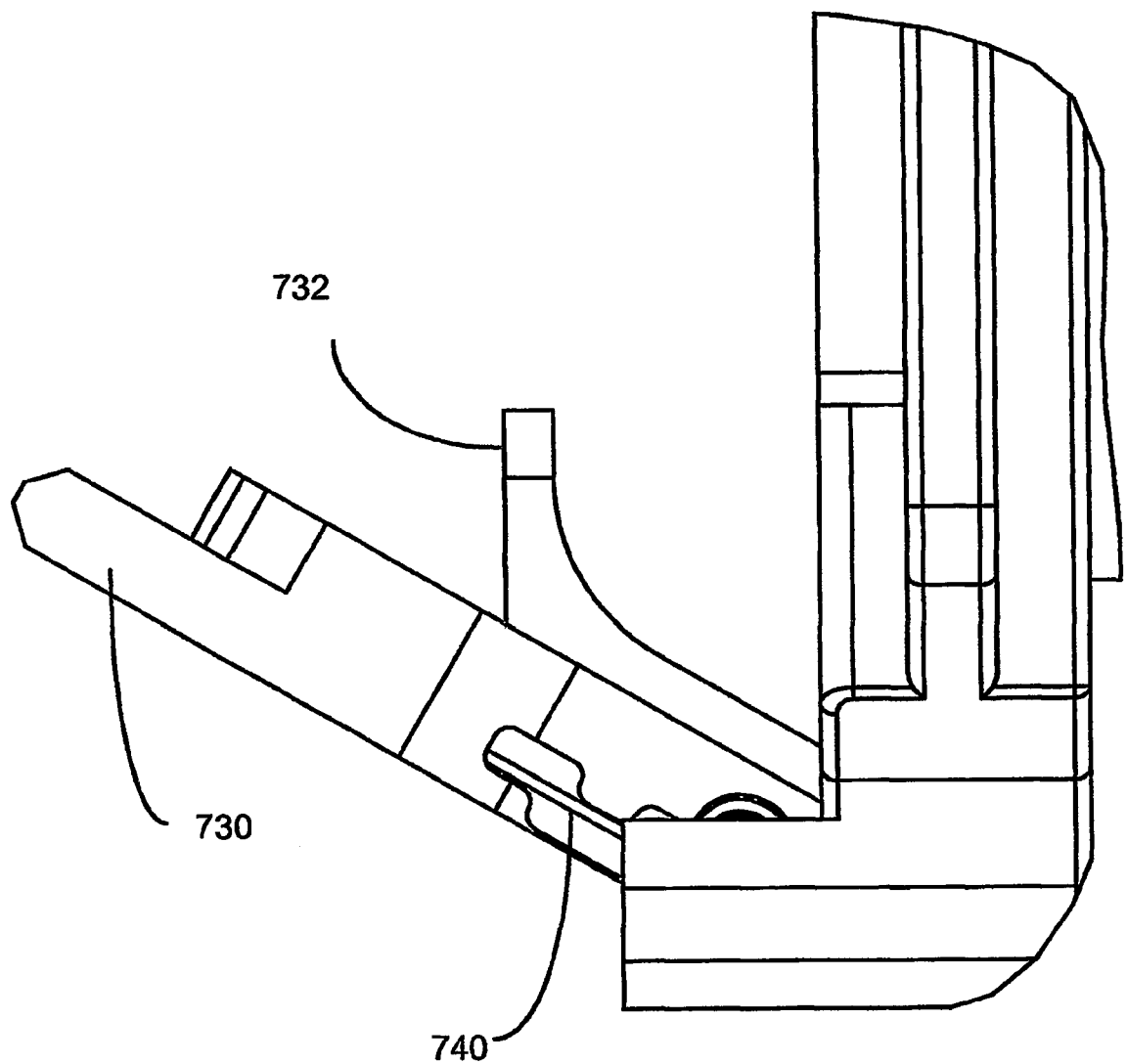
FIG. 7G illustrates a side view of the adapter portion of FIG. 7F.

As best illustrated in FIGS. 7F and 7G, retaining member 730 can be biased in an open position using, for example, a spring loaded extension arm 740 attached to or in operative connection with retaining member 730. In this embodiment, when retaining member 720 is slid upward or radially outward to release retaining member 730 and syringe 200 is removed, retaining member 730 is biased in an open or receiving position to receive another syringe.

Figure 8A:
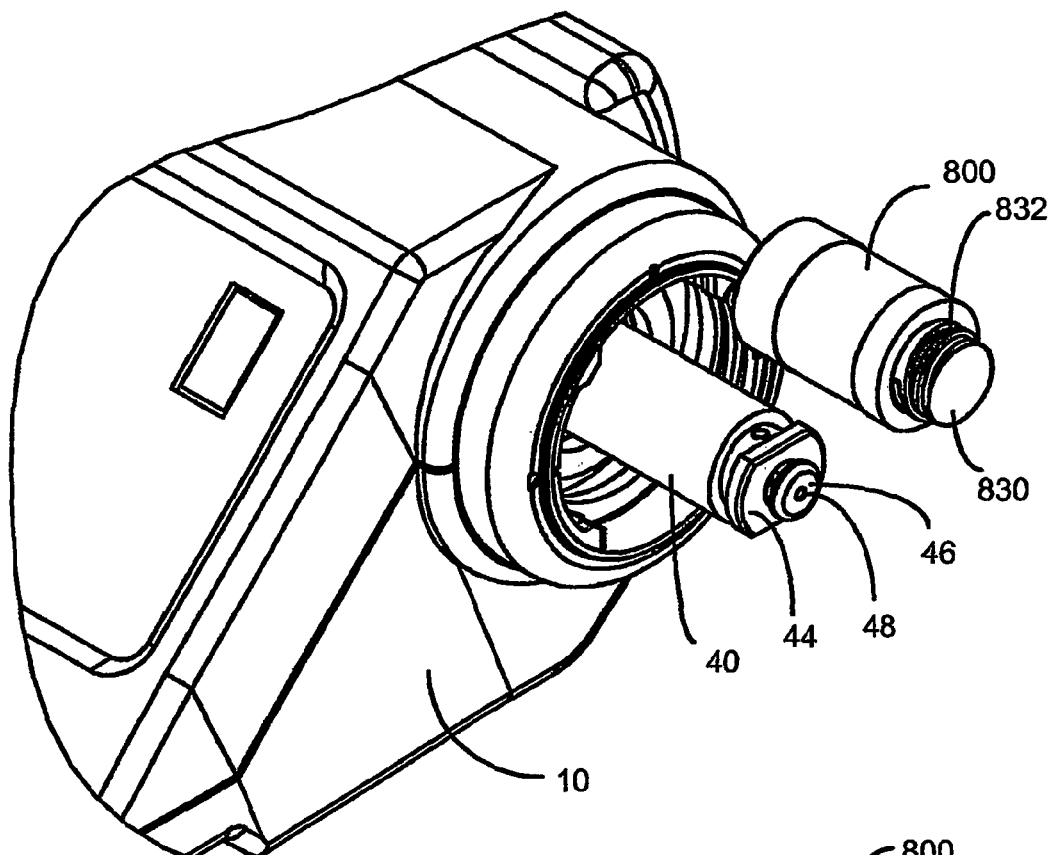
FIG. 8A illustrates a perspective view of the injector of FIG. 1 and a plunger adapter for connection to the piston thereof in a disconnected state.
Figure 8B:
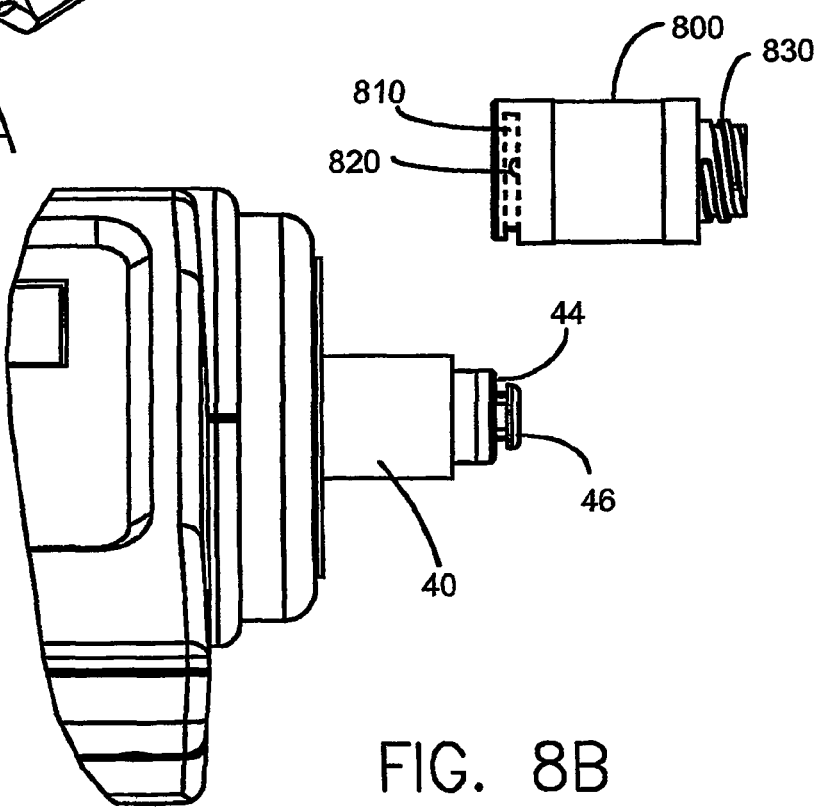
FIG. 8B illustrates a side view of the injector and the plunger adapter of FIG. 8A in a disconnected state.
Figure 8C:
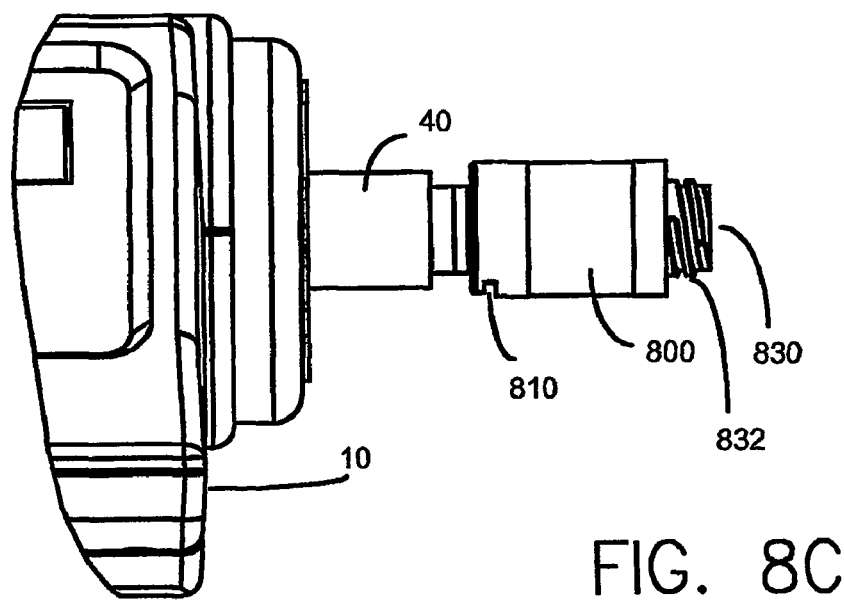
FIG. 8C illustrates a side view of the injector and the plunger adapter of FIG. 8A in a connected state.
Figure 8D:
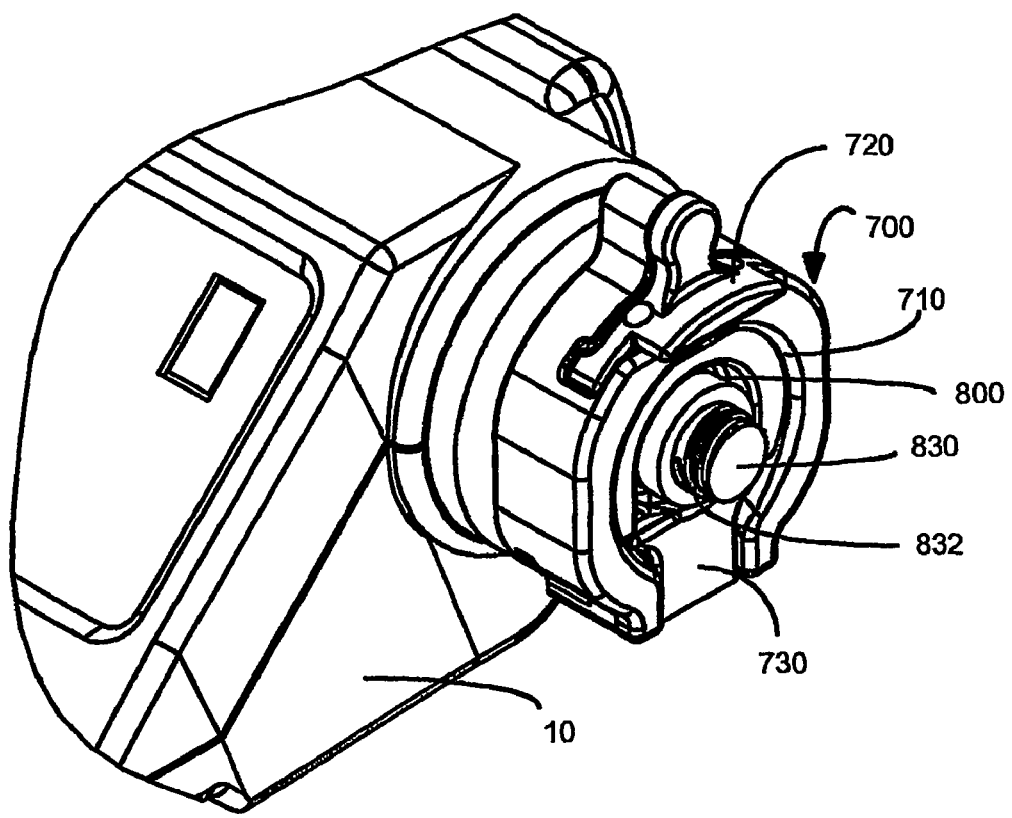
FIG. 8D illustrates a perspective view of the injector and the plunger adapter of FIG. 8A, and the syringe adapter of FIG. 7A in a connected state.
Figure 8E:
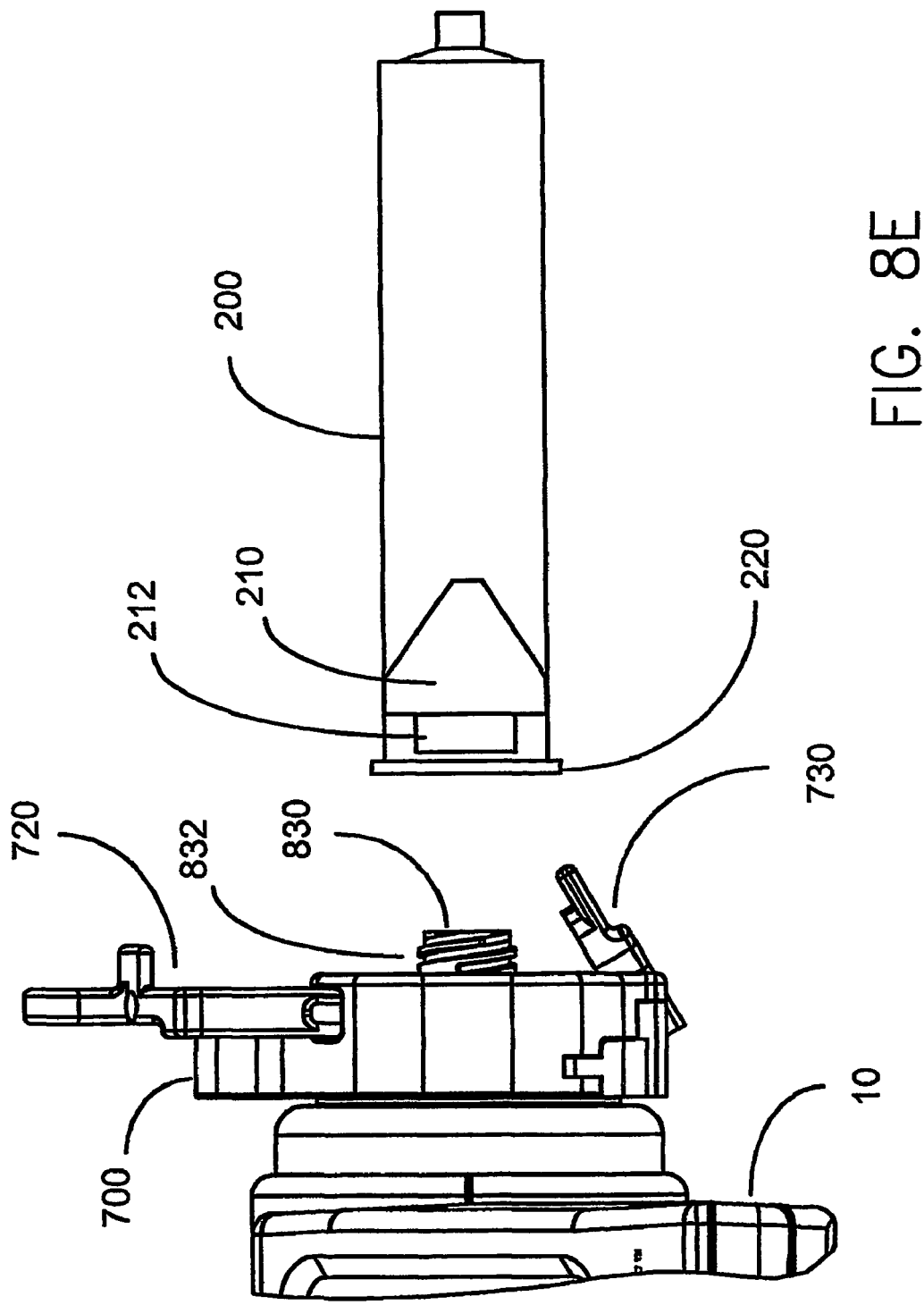
FIG. 8E illustrates a side view of the injector and the plunger adapter of FIG. 8A, and the syringe adapter of FIG. 7A in a connected state with a syringe aligned for connection therewith.

As briefly discussed above, in performing an injection procedure with the syringe interfaces and adapters of the present invention, it is typically necessary to make a connection with a plunger such as, for example, syringe plunger 210 (see, for example, FIG. 8E). It is thus often necessary to provide a plunger adapter 800 as illustrated in FIG. 8A to adapt piston 40 for use with a plunger type used in a particular syringe to be adapted for use with injector 10. FIGS. 8A through 8E illustrate the use of a plunger adapter 800 with injector 10, syringe 200 (including plunger 210) and syringe adapter 700 (as discussed in connection with FIGS. 7A through 7G). As best illustrated in FIGS. 8A and 8B, piston 40 includes a flanged extension 46 on piston flange 44. Plunger adapter 800 includes a slot 810 adapted to receive flanged extension 46 therein to attach plunger adapter 800 to piston 40 as illustrated, for example, in FIG. 8C. Flanged extension 46 can also include a depression 48 that cooperates with a biased detent mechanism in slot 810 (for example, a spring-loaded ball 820) to assist in forming a secure connection between plunger adapter 800 and piston 40.

FIG. 8D illustrates injector 10 with syringe adapter 700 and plunger adapter 800 attached thereto. Plunger adapter 800 includes on the forward end thereof an attachment mechanism 830 for forming a connection with a capture member 212 on the rearward portion of plunger 210 (see FIGS. 7C and 8E). In the embodiment of FIGS. 8A-8E, plunger attachment mechanism 830 includes threading 832 that cooperates with mating threading on the interior of plunger capture member 212.

The attachment of syringe 200 proceeds generally as discussed above. In addition, however, as syringe flange 220 makes contact with contact member 732 of second retaining member 730, threaded plunger attachment mechanism 830 preferably also comes into contact with threaded plunger capture member 212. At this point, the user can rotate syringe 200 about its axis so that attachment mechanism 830 and capture member 212 form a secure connection. Rotating syringe 200 also causes syringe 200 to move rearward as attachment mechanism 830 is threaded onto capture member 212. Piston 40 and plunger adapter 800 are preferably properly positioned (using, for example, an appropriate positioning setting on injector 10), and syringe adapter 700, attachment mechanism 830 and capture member 212 are preferably properly dimensioned such that when plunger attachment mechanism 830 and capture member 212 are fully connected, syringe 220 has moved rearward into the position of FIGS. 7D and 7E. Once again, in this position, second retaining member 730 has pivoted to a generally vertical position. In this position, retaining member 720 can be slid radially inward to a closed position to secure syringe 200 within adapter 700. Plunger adapter 800 is also suitable for use with the other syringe adapters discussed above.

As clear to one skilled in the art, the syringe interfaces and adapters of the present invention can be reconfigured and attached to a wide variety of front-loading injectors simply through modification of the rearward attachment mechanism of the syringe adapters. In that regard, FIG. 9A illustrates another embodiment of a syringe adapter 700' which is similar in operation to syringe adapter 700, except for the manner in which adapter 700' is attached to an injector syringe interface/release mechanism 4010, which is illustrated in FIGS. 9B and 9C.

Release mechanism 4010 includes a connector housing 4024 which contains at least two elements that facilitate connection of syringe adapter 700' to an injector 4014. The first element is a flex ring 4026 disposed within release mechanism 4010 near front end 4020. The second element is a rotating ring 4028 disposed within release mechanism 4010 near rearward end 4016. Flex ring 4026 and rotating ring 4028 are adapted to cooperate with one another, as described in greater detail below, to permit connection and release of syringe adapter 700' (and, accordingly, syringe 200) to and from release mechanism 4010 (and, accordingly, to and from injector 4014). Injector 4014 and release mechanism 4010 are described in detail in PCT Publication No. WO 01/37903 and U.S. patent application Publication No. 2001-47153, the contents of which are hereby incorporated by reference.

Figure 9A:
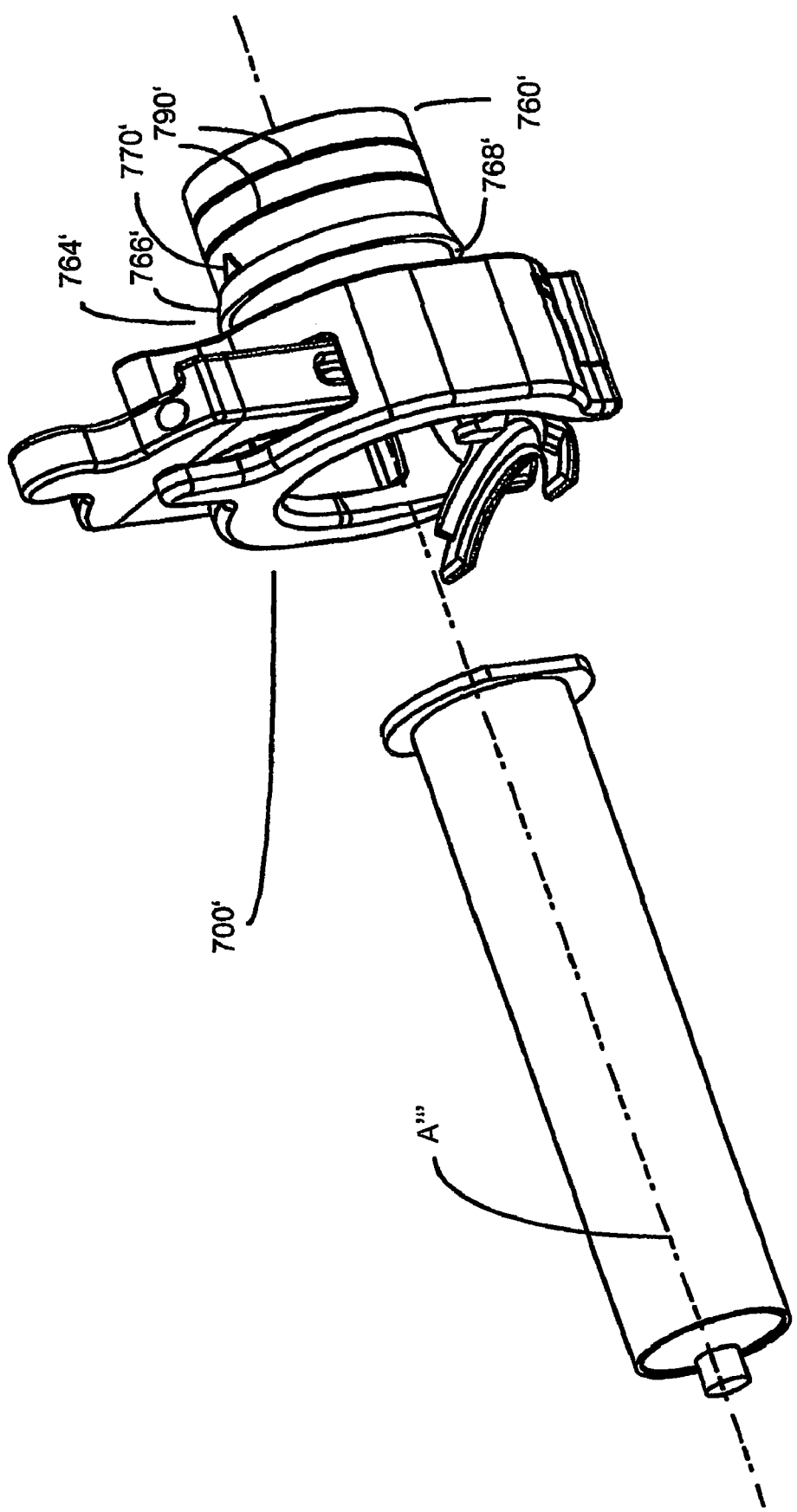
FIG. 9A illustrates a perspective view of another embodiment of a syringe and a syringe adapter similar to that of FIG. 7A in which the syringe and syringe adapter are in a disconnected state and the syringe adapter includes an alternative mechanism for releasable attachment to the injector of FIGS. 9B and 9C.
Figure 9B:
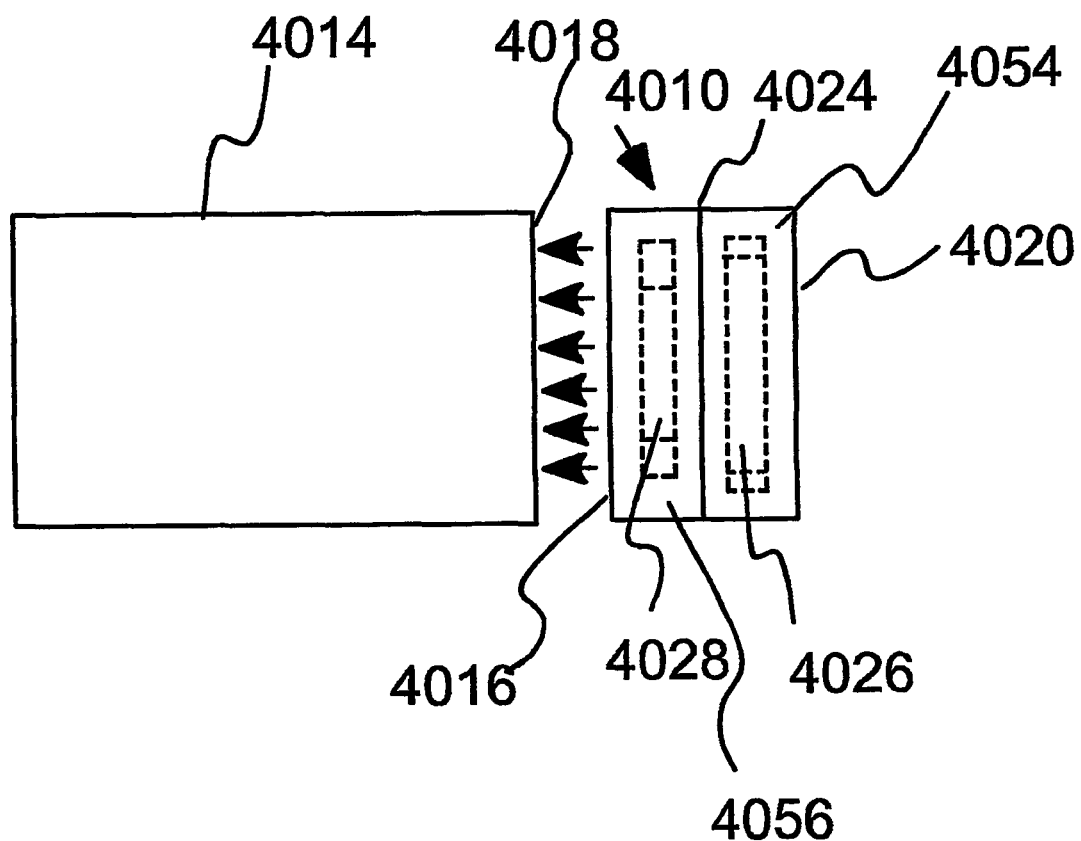
FIG. 9B illustrates a side view of an embodiment of an injector release/connector mechanism for use with the adapter of FIG. 9A.
Figure 9C:
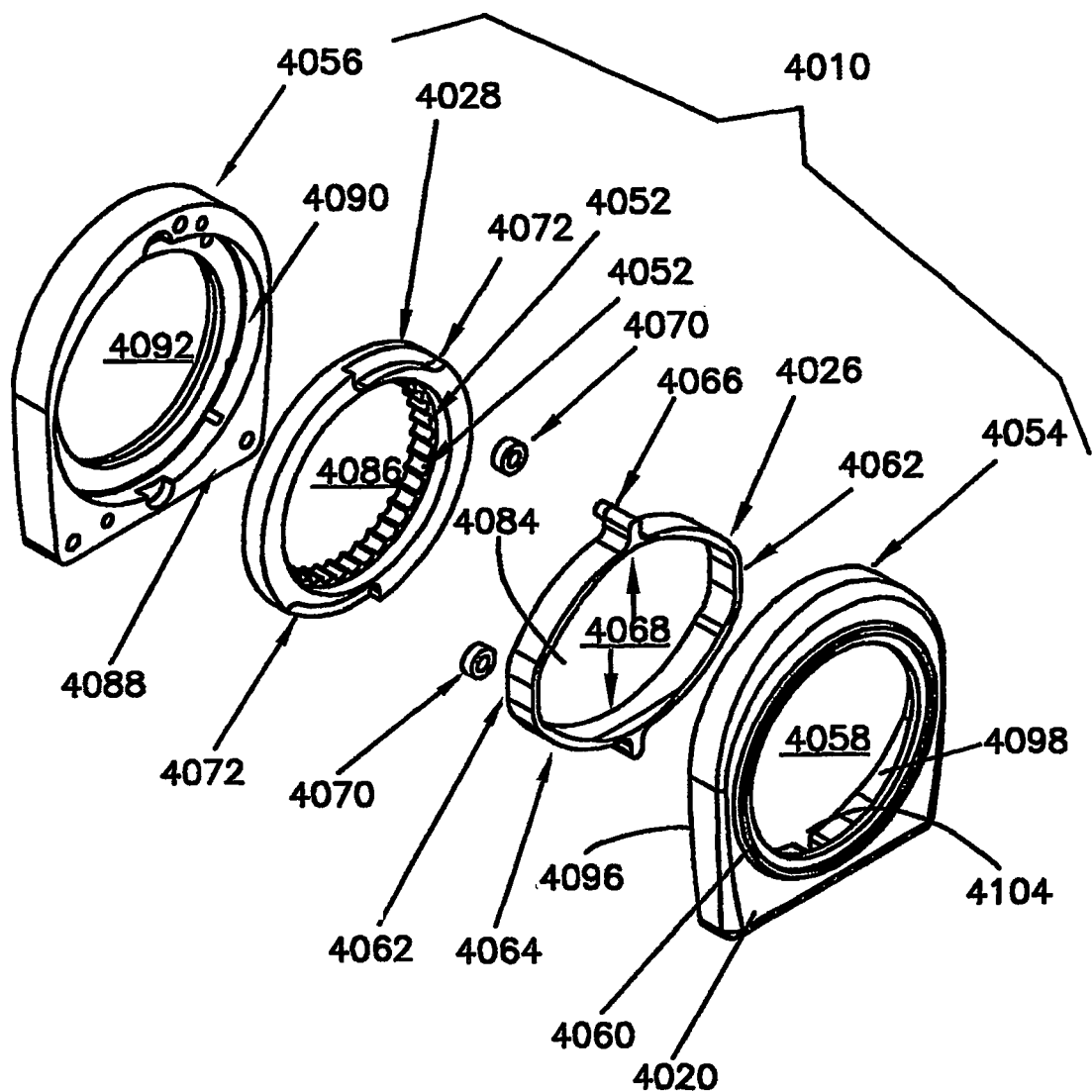
FIG. 9C illustrates a perspective view of the release/connector mechanism of FIG. 9B.

As shown in FIG. 9A, a flange or ridge 764' is preferably integrally formed on syringe adapter 700' toward rearward end 760' of syringe adapter 700'. Ridge 764' includes two parts, a sloping section 766' and a shoulder section 768' that is essentially perpendicular to axis A''' around which syringe adapter 700' is formed (although, not necessarily symmetrically therearound). At least one, and preferably two or more, extending tabs or projections 770' are provided at rearward end 760' of syringe adapter 700'. Tabs 770' engage grooves 4052 (see, for example, FIG. 9C) provided in ring 4028 as discussed below. Alternatively, and as clear to those skilled in the art, slots, recesses or divots, etc., could be provided in rear end 760' of syringe adapter 700' and cooperating tabs or projections could be provided on the interior surface of rotating ring 4028.

Release/connector mechanism 4010 includes, for example, a front plate 4054 and a rear plate 4056. Front plate 4054 and rear plate 4056 can, for example, be constructed of aluminum coated with a fluoropolymer (such as Tufram™, which is the product name of a fluoropolymer manufactured by the General Magna Plate Company). The fluoropolymer coating provides improved resistance to wear and also provides lubricity to the exterior surfaces of front plate 4054 and rear plate 4056. Lubricity is particularly advantageous because, when contrast medium crystallizes on the exterior surface of front plate 4054 or rear plate 4056, it easily flakes off of the surface when the surface is coated with the fluoropolymer. Of course, any suitable alternative coating material may be used on the exterior surface of front plate 4054 or rear plate 4056.

As clear to one skilled in the art, a coating may not need to be applied to the surface of front plate 4054 or rear plate 4056 if either plate is made of a suitable material. For example, if front plate 4054 and rear plate 4056 are constructed of a high density plastic (an acetyl copolymer, for example) the material itself can provide resistance to caking of contrast media, similar to the fluoropolymer coating on aluminum.

As shown in FIG. 9C, front plate 4054 defines a hole or passage 4058 therethrough. A lip 4060 extends around the periphery of hole 4058 through front plate 4054 to abut syringe adapter 700'. Flex ring 4026 is a substantially elliptically shaped member that is disposed behind front plate 4054 of release/connector mechanism 4010. Flex ring 4026 can, for example, be made from an acetal copolymer or any other suitable material. Flex ring 4026 includes, on either side, a linear or flattened portion 4062 that is integrally connected to two curved portions 4064. From approximately the midpoint of curved portions 4064, posts 4066 extend toward rear plate 4056. As shown, flex ring 4026 defines a hole or passage 4068 therethrough. On a front end of flex ring 4026, a chamfered surface is preferably provided. The chamfered surface facilitates insertion of rear end 760' and ridge 764' of syringe adapter 700' therethrough.

In the embodiment illustrated in FIG. 9C, posts 4066 extending rearward from flex ring 4026 are provided with bearings 4070. Bearings 4070 preferably are composite bearings (for example, metal and plastic) having inner and outer races with roller bearings disposed therebetween. Alternatively, bearings 4070 may be plastic elements that surround posts 4066 and rotate with respect thereto. Bearings 4070 engage grooves or cam tracks 4072 on rotating ring 4028. As clear to those skilled in the art, however, bearings are not required for the operation of release/connector mechanism 4010.

Rotating ring 4028, which is disposed to the rear of flex ring 4026 within housing 4024, includes two grooves or cam tracks 4072 on a front surface 4074 thereof as discussed above. Cam tracks 4072 are shaped such that the outer surface thereof increases in diameter along its arc from a closest point to the center of rotating ring 4028 to a farthest point from the center of ring 4028. Grooves 4072 engage posts 4066 through bearings 4070 and, when syringe adapter 700' is rotated while engaging rotating ring 4028 (for example, to disengage syringe adapter 700' from release/connector mechanism 4010), force posts 4066 apart to stretch flex ring 4026 in a direction indicated by arrows 4084. As shown, flex ring 4026 has a hole 4068 through its center to accommodate rearward end 760' of syringe adapter 700' therein or therethrough.

Rotating ring 4028 is disposed within an indentation or recess 4090 formed in front surface 4088 of rear plate 4056. Rear plate 4056 defines a hole or passage 4092 therethrough for accommodating rear portion 760' of syringe adapter 700'. Rotating ring 4028 is disposed in indentation 4090 so that ring 4028 may freely rotate therein.

Rear surface 4096 of front plate 4054 includes an indentation or recess 4098 that has essentially the same shape as flex ring 4026. As such, indentation 4098 includes two linear or flattened portions and two curved portions. Two notches 4104 (only one of which is illustrated in FIG. 9C) in rear surface 4096 of front plate 4054 are positioned at approximately the center point of the curved sections. Notches 4104 accommodate posts 4066 and the associated structures that connect posts 4066 to flex ring 4026. Indentation 4098 is shaped to be larger than flex ring 4026 and the distance between notches 4104 is greater than the distance between posts 4066 in their relaxed state. Notches 4104 help to prevent flex ring 4026 from rotating within housing 4024 and permit flex ring 4026 to expand upon rotation of rotating ring 4028.

During connection of syringe adapter 700', rearward end 760' of syringe adapter 700' is inserted into connector housing 4024 through hole or interface 4058 in front plate 4054. Flex ring 4026 sits within indentation 4098 formed in rear surface 4096 of front plate 4054 so that posts 4066 engage notches 4104. Therefore, when inclined surface 766' of ridge 764' of syringe adapter 700' engages the chamfers on flex ring 4026, ridge 764' pushes open flex ring 4026 in direction 4084 from its relaxed distance to its extended distance.

After ridge 764' clears the rear edge of flex ring 4026, the elastic nature of flex ring 4026 causes flex ring 4026 to resume its relaxed state in the direction opposite of arrows 4084. When flex ring 4026 resumes its relaxed state, shoulder 768' of ridge 764' engages the rear edge of flex ring 4026. Syringe adapter 700' is thereby held in place by flex ring 4026 and cannot be axially removed from release/connector mechanism 4010. When flex ring 4026 resumes its relaxed state, it preferably provides an audible "click" to indicate to the operator that syringe adapter 700' has been installed on injector 4014.

Removal of syringe adapter 700' from release/connector mechanism 4010 in the embodiment of FIGS. 9B and 9C requires that syringe adapter 700' be rotated ¼ turn or an approximate one quarter turn, as described below. Once syringe adapter 700 has been engaged by flex ring 4026, projections 770' engage grooves 4052 in rotating ring 4028. As syringe adapter 700' is rotated, for example, approximately one quarter turn in, for example, the counter-clockwise direction, projections 770', which engage grooves 4052, force rotating ring 4028 also to rotate approximately the same amount in the same direction. Alternately, any suitable range of rotation and/or the opposite rotational direction can be used to facilitate disengagement of syringe adapter 700' from mechanism 4010.)

Because posts 4066 (with bearings 4070) of flex ring 4026 engage and ride along cam tracks 4072 on rotating ring 4028, the rotation of ring 4028 will urge flex ring 4026 from its relaxed (i.e., syringe adapter engaged) state to its extended (i.e., syringe adapter disengaged) state. As posts 4066 travel along cam tracks 4072 from the inner-most position to the outermost position, flex ring 4026 is stretched from the relaxed state to the extended distance state, at which point the rear edge of flex ring 4026 disengages shoulder 768' of syringe adapter 700'. Consequently, syringe adapter 700' is disengaged and may be axially removed from flex ring 4026 and mechanism 4010. When syringe adapter 700 is removed from mechanism 4010, the spring force of flex ring 4026 urges posts 4066 to travel along cam tracks 4072 from the outer-most position to the inner-most position, thereby returning flex ring 4025 to its relaxed state for receipt of a new syringe or syringe adapter. In addition, when syringe adapter 700' is disengaged from flex ring 4026, the operator preferably hears a second audible "click" to indicate that syringe adapter 700 has been disengaged from mechanism 4010 (and, accordingly, from injector 4014).

The rearward portion of syringe adapter 700' includes indicators 790' that can cooperate with a light source and sensors (not shown) as described in U.S. patent application Ser. No. 09/796,498, filed on Jan. 18, 2001, assigned to the assignee of the present invention, the disclosure of which is incorporated herein by reference, to provide information about the configuration of syringe 300.

FIGS. 10A-10C illustrate another embodiment of a syringe adapter 900 of the present invention including a syringe interface in which a sliding retaining member 920 includes a plurality of inward extending abutment members 930a and 930b on each of two lateral sides thereof. Each of the abutment members 930a and 930b is connected to adjacent abutment members by a hinge mechanism 932a and 932b, respectively, such that adjacent abutment members can move, hinge or rotate relative to each other. In the embodiment of FIGS. 10A through 10C, hinges 932a and 932b can be areas of relatively thin width such as known for formation of plastic hinges. Additionally, hinges 932a and 932b can be narrow gaps between abutment members 930a and 930b, respectively, with flexible connective members 940a and 940b connecting abutment members 930a and 930b, respectively. Connective members 940a and 940b can act as flanges that seat in a curved or arced channel 950 through which flanges 940a and 940b slide as retaining member 920 is moved up and down (radially) in a plane generally perpendicular to the axis of syringe 200.

As retaining member 920 is slid downward in a passage 924 formed in adapter 900, abutment members 930a and 930b rotate or hinge relative to each other as connective members 940a and 940b slide through curved or arced channel 950 to form a circumferential abutment for syringe flange 220 as illustrated in FIGS. 10B and 10C. As illustrated in FIGS. 10A and 10B, an arched or U-shaped portion 926 of retaining member 920 can form an abutment with an upper half of syringe flange 220 while abutment members 930a and 930b form an abutment with a lower half of syringe flange 220 to abut the entire circumference of syringe flange 220. Alternately, however, the U-shaped portion 926 and the abutment members 930a and 930b could be configured in such a manner that they abut less than the entire circumference of syringe flange 220.

As described above, adapter 900 can include an injector attachment mechanism including, for example, flanges 960a and 960b for attachment to a powered injector such as injector 10. As also described above, other types of attachment mechanisms for attachment to other powered injectors can be used in connection with the syringe interface of adapter 900. Moreover, like the other syringe interfaces or retaining mechanisms of the adapters of the present invention, the syringe interface of adapter 900 can be permanently affixed to a powered injector.

FIG. 11 illustrates an alternative embodiment of a retaining member 920' that operates in a similar manner to retaining member 920. In retaining member 920', each abutment member 930a' is connected to adjacent abutment members 930a' via a ball and socket joint 932a. Each of abutment members 930a' includes an outer flange 940a' that seats in a curved or arced channel such as channel 950 described above.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A method of attaching a syringe comprising a flange to an injector, the method comprising:
providing an injector comprising: a mounting mechanism on a front of the injector; a piston reciprocally movable through the mounting mechanism; and an adapter operable to attach a syringe comprising a flange to the adapter, the adapter comprising: a rear portion comprising an attachment mechanism adapted to attach the adapter to the mounting mechanism of the injector; a first retaining member that pivots about an axis generally perpendicular to and offset from the axis of the piston when the adapter is attached to the injector, the first retaining member pivoting in a rearward direction to engage a portion of the syringe flange; and a second retaining member slideably positioned within a passage in the adapter to slide in a direction generally perpendicular to the axis of the piston when the adapter is attached to the injector to engage a portion of the syringe flange;
inserting the syringe flange into the adapter;
pivoting the first retaining member about an axis generally perpendicular to and offset from the axis of the injector piston to engage a portion of the syringe flange; and
moving the second retaining member in a direction generally perpendicular to an axis of an injector piston to engage at least a portion of the syringe flange.

2. The method of claim 1, further comprising:
rotating the syringe to attach a plunger of the syringe to the injector piston.

3. An injector comprising:
a mounting mechanism on a front of the injector;
a piston reciprocally movable through the mounting mechanism; and
an adapter operable to attach a syringe comprising a flange to the adapter, the adapter comprising:
a rear portion comprising an attachment mechanism adapted to attach the adapter to the mounting mechanism of the injector;
a first retaining member that pivots about an axis generally perpendicular to and offset from the axis of the piston when the adapter is attached to the injector, the first retaining member pivoting in a rearward direction to engage a portion of the syringe flange; and
a second retaining member slideably positioned within a passage in the adapter to slide in a direction generally perpendicular to the axis of the piston when the adapter is attached to the injector to engage a portion of the syringe flange.

4. The injector of claim 3 wherein the attachment mechanism comprises one or more mounting flanges.

5. The injector of claim 4 wherein the attachment mechanism further comprises at least one extending projection.

6. The injector of claim 3 wherein the adapter further comprises one or more indicators operable to provide information about the syringe to the injector.

7. The injector of claim 3 wherein the first retaining member and the second retaining member cooperate to engage the syringe flange around the entire perimeter of the syringe flange.

8. The injector of claim 3 wherein the first retaining member is biased toward an open position.

9. The injector of claim 3, further comprising a contact member operably associated with the first retaining member, the contact member operable to cause the first retaining member to pivot about the axis generally perpendicular to and offset from the axis of the piston.

10. The injector of claim 3 wherein the second retaining member comprises a generally U-shaped abutment member operable to engage at least a portion of the syringe flange.

11. An injector comprising:

a mounting mechanism on a front of the injector;

a piston reciprocally movable through the mounting mechanism; and a syringe interface operable to attach a syringe comprising a flange to the syringe interface, the syringe interface comprising:

a rear portion comprising an attachment mechanism adapted to attach the syringe interface to the mounting mechanism of the injector;

a first retaining member that pivots about an axis generally perpendicular to and offset from the axis of the piston when the syringe interface is attached to the injector, the first retaining member pivoting in a rearward direction to engage a portion of the syringe flange; and a second retaining member slideably positioned within a passage in the syringe interface to slide in a direction generally perpendicular to the axis of the piston when the syringe interface is attached to the injector to engage a portion of the syringe flange.

12. The injector of claim 11 wherein the attachment mechanism comprises one or more mounting flanges.

13. The injector of claim 12 wherein the attachment mechanism further comprises at least one extending projection.

14. The injector of claim 11 wherein the syringe interface further comprises one or more indicators operable to provide information about the syringe to the injector.

15. The injector of claim 11 wherein the first retaining member and the second retaining member cooperate to engage the syringe flange around the entire perimeter of the syringe flange.

16. The injector of claim 11, wherein the first retaining member is biased toward an open position.

17. The injector of claim 11, further comprising a contact member operably associated with the first retaining member, the contact member operable to cause the first retaining member to pivot about the axis generally perpendicular to and offset from the axis of the piston.

18. The injector of claim 11 wherein the second retaining member comprises a generally U-shaped abutment member operable to engage at least a portion of the syringe flange.

19. An injector comprising:

a mounting mechanism on a front of the injector;

a piston reciprocally movable through the mounting mechanism; and an adapter operable to attach a syringe comprising a flange to the adapter, the adapter comprising:

a rear portion comprising an attachment mechanism adapted to attach the adapter to the mounting mechanism of the injector, the attachment mechanism comprising one or more mounting flanges;

a first retaining member that pivots about an axis generally perpendicular to and offset from the axis of the piston when the adapter is attached to the injector, the first retaining member pivoting in a rearward direction to engage a portion of the syringe flange; and a second retaining member slideably positioned within a passage in the adapter to slide in a direction generally perpendicular to the axis of the piston when the adapter is attached to the injector to engage a portion of the syringe flange.

20. An injector comprising:

a mounting mechanism on a front of the injector;

a piston reciprocally movable through the mounting mechanism; and an adapter operable to attach a syringe comprising a flange to the adapter, the adapter comprising:

a rear portion comprising an attachment mechanism adapted to attach the adapter to the mounting mechanism of the injector;

a first retaining member that pivots about an axis generally perpendicular to and offset from the axis of the piston when the adapter is attached to the injector, the first retaining member pivoting in a rearward direction to engage a portion of the syringe flange; and a second retaining member slideably positioned within a passage in the adapter to slide in a direction generally perpendicular to the axis of the piston when the adapter is attached to the injector to engage a portion of the syringe flange;

wherein the first and second retaining members cooperate to engage the syringe flange around the perimeter of the syringe flange.

21. An injector comprising:

a mounting mechanism on a front of the injector;

a piston reciprocally movable through the mounting mechanism; and an adapter operable to attach a syringe comprising a flange to the adapter, the adapter comprising:

a rear portion comprising an attachment mechanism adapted to attach the adapter to the mounting mechanism of the injector;

a first retaining member that is biased toward an open position and pivots about an axis generally perpendicular to and offset from the axis of the piston when the adapter is attached to the injector, the first retaining member pivoting in a rearward direction to engage a portion of the syringe flange; and a second retaining member slideably positioned within a passage in the adapter to slide in a direction generally perpendicular to the axis of the piston when the adapter is attached to the injector to engage a portion of the syringe flange.

22. A method of attaching a syringe comprising a flange to an injector, the method comprising:

providing an injector comprising: a mounting mechanism on a front of the injector; a piston reciprocally movable through the mounting mechanism; and a syringe interface operable to attach a syringe comprising a flange to the syringe interface, the syringe interface comprising: a rear portion comprising an affachment mechanism adapted to attach the syringe interface to the mounting mechanism of the injector; a first retaining member that pivots about an axis generally perpendicular to and offset from the axis of the piston when the syringe interface is attached to the injector, the first retaining member pivoting in a rearward direction to engage a portion of the syringe flange; and a second retaining member slideably positioned within a passage in the syringe interface to slide in a direction generally perpendicular to the axis of the piston when the syringe interface is attached to the injector to engage a portion of the syringe flange;

inserting the syringe flange into the syringe interface;
pivoting the first retaining member about an axis generally perpendicular to and offset from the axis of the injector piston to engage a portion of the syringe flange; and moving the second retaining member in a direction generally perpendicular to an axis of an injector piston to engage at least a portion of the syringe flange.

\* \* \* \* \*

UNITED STATES PATENT AND TRADEMARK OFFICE
CERTIFICATE OF CORRECTION

PATENT NO. : 7,273,477 B2  
APPLICATION NO. : 10/466413  
DATED : September 25, 2007  
INVENTOR(S) : Spohn et al.

It is certified that error appears in the above-identified patent and that said Letters Patent is hereby corrected as shown below:

IN THE SPECIFICATION  
In Column 10, Line 16, delete "fill" and insert -- full --, therefor.

IN THE CLAIMS  
In Column 17, Line 36, in Claim 16, after "claim 11" delete ",".  
In Column 18, Line 55, in Claim 22, delete "affachment" and insert -- attachment --, therefor.

Signed and Sealed this

Tenth Day of June, 2008

JON W. DUDAS  
*Director of the United States Patent and Trademark Office*